United States Patent
Lerner et al.

(10) Patent No.: US 6,231,888 B1
(45) Date of Patent: *May 15, 2001

(54) LOCAL DELIVERY OF NON STEROIDAL ANTI INFLAMMATORY DRUGS (NSAIDS) TO THE COLON AS A TREATMENT FOR COLONIC POLYPS

(75) Inventors: E. Itzhak Lerner; Moshe Flashner, both of Petah Tikva; Adel Penhasi, Bat-Yam, all of (IL)

(73) Assignee: Perio Products Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/190,127

(22) Filed: Nov. 12, 1998

Related U.S. Application Data

(63) Continuation-in-part of application No. 08/588,247, filed on Jan. 18, 1996, now Pat. No. 5,840,332.

(51) Int. Cl.⁷ ........................................ A61K 9/20
(52) U.S. Cl. ................ 424/463; 424/489; 424/468; 424/497; 424/486; 424/450; 424/463; 424/473
(58) Field of Search .................... 424/464, 465, 424/489, 400, 473, 482, 463, 452, 497; 514/449

(56) References Cited

U.S. PATENT DOCUMENTS

| | | | |
|---|---|---|---|
| 3,921,636 | 11/1975 | Zaffaroni | 128/260 |
| 4,016,100 | 4/1977 | Suzuki et al. | 252/316 |
| 4,107,288 | 8/1978 | Oppenheim et al. | 424/22 |
| 4,138,362 | 2/1979 | Vassiliades et al. | 252/316 |
| 4,169,804 | 10/1979 | Yapel, Jr. | 252/62.53 |
| 4,169,885 | 10/1979 | Raaf et al. | 424/16 |
| 4,277,364 | 7/1981 | Shasha et al. | 252/316 |
| 4,279,812 | 7/1981 | Cioca | 260/123.7 |
| 4,307,717 | 12/1981 | Hymes et al. | 128/156 |
| 4,344,857 | 8/1982 | Shasha et al. | 252/316 |
| 4,348,384 | 9/1982 | Horikoshi et al. | 424/101 |
| 4,349,530 | 9/1982 | Royer | 424/19 |
| 4,359,483 | 11/1982 | Kaetsu et al. | 427/2 |
| 4,442,655 | 4/1984 | Stroetmann | 53/428 |
| 4,492,684 | 1/1985 | Goosen et al. | 424/19 |
| 4,568,536 | 2/1986 | Kronenthal et al. | 424/22 |
| 4,569,837 | 2/1986 | Suzuki et al. | 424/28 |
| 4,619,913 | 10/1986 | Luck et al. | 514/2 |
| 4,675,381 | 6/1987 | Bichon | 530/345 |
| 4,678,516 | 7/1987 | Alderman et al. | 106/197.1 |
| 4,703,108 | 10/1987 | Silver et al. | 530/356 |
| 4,794,002 | 12/1988 | Henis et al. | 424/488 |
| 4,803,075 | 2/1989 | Wallace et al. | 424/423 |
| 5,401,774 | 3/1995 | Pamukcu et al. | 514/569 |
| 5,422,121 | 6/1995 | Lehmann et al. | 424/464 |
| 5,464,633 | 11/1995 | Conte et al. | 424/480 |
| 5,498,608 | 3/1996 | Johnson et al. | 514/150 |
| 5,514,663 | 5/1996 | Mandel | 514/33 |
| 5,525,634 | 6/1996 | Sintov et al. | 514/777 |
| 5,622,948 | 4/1997 | Dunn et al. | 514/236.5 |
| 5,631,022 | 5/1997 | Mandel et al. | 424/456 |
| 5,643,959 | 7/1997 | Pamukcu et al. | 514/569 |
| 5,651,983 | 7/1997 | Kelm et al. | 424/452 |
| 5,656,290 | 8/1997 | Kelm et al. | 424/456 |
| 5,679,638 | 10/1997 | Teicher et al. | 514/6 |
| 5,686,105 | 11/1997 | Kelm et al. | 424/452 |
| 5,686,106 | 11/1997 | Kelm et al. | 424/463 |
| 5,686,589 | 11/1997 | Brendel et al. | 536/20 |
| 5,795,909 | 8/1998 | Shashoua et al. | 514/449 |
| 5,840,332 | 11/1998 | Lerner et al. | 424/464 |

FOREIGN PATENT DOCUMENTS

| | | |
|---|---|---|
| 0 485 157 A2 | 5/1992 | (EP) . |
| 0 485 158 A2 | 5/1992 | (EP) . |
| 0 485 171 A2 | 5/1992 | (EP) . |
| 0 485 172 A2 | 5/1992 | (EP) . |
| 0 485 173 A2 | 5/1992 | (EP) . |
| 0 508 586 A1 | 10/1992 | (EP) . |
| 0 595 110 A1 | 4/1994 | (EP) . |
| WO 91/07949 | 6/1991 | (WO) . |
| WO 92/00732 | 1/1992 | (WO) . |
| 97/03659 | 2/1997 | (WO) . |

OTHER PUBLICATIONS

"Adverse Effects of Sulindac Used for Prevention of Colorectal Cancer," *Journal of the National Cancer Institute.* 89 (18):1381 (Sep. 17, 1997).

Waverly, Z. et al., "Pectin/Ethylcellulose Film Coating Formulations for Colonic Drug Delivery," *Pharm. Res.* 13(8):1210–1212 (Aug. 1996).

Derwent World Patents Index, Dialog File 351, WPI Accession No. 94–145315/199418, Abstract of EP 0 595 110 A1.

Adkin, D.A. et al., "The Use of Scintigraphy to Provide "Proof of Concept" for Novel Polysaccharide Preparations Designed for Colonic Drug Delivery," *Pharm. Res.* 14(1):103–107 (Jan. 1997).

Bedi, A. et al., "Inhibition of Apoptosis during Development of Colorectal Cancer," *Cancer Res.* 55(9):1811–1816 (1995).

Bright, J.J. and A. Khar, "Apoptosis: Programmed Cell Death in Health and Disease," *Bioscience Reports* 14(2):67–81 (1994).

Brogden, R.N. et al., "Sulindac: A Review of its Pharmacological Properties and Therapeutic Efficacy in Rheumatic Diseases," *Drugs* 16(2):97–114 (1978).

Craven, P.A. and F.R. DeRubertis, "Effects of aspirin on 1,–2–dimethylhydrazine–induced colonic carcinogenesis," *Carcinogenesis* 13(4):541–546 (1992).

(List continued on next page.)

Primary Examiner—Thurman K. Page
Assistant Examiner—Blessing Fubara
(74) Attorney, Agent, or Firm—D 'Vorah Graeser

(57) ABSTRACT

A composition and method for the treatment of polyp and colon cancer is described, such composition and method providing for the colonic delivery and/or preferential metabolism of a drug or desired agent, especially an NSAID, in the colon of the patient in need such treatment.

61 Claims, 3 Drawing Sheets

OTHER PUBLICATIONS

Davis, S.S. et al., "Transit of pharmaceutical dosage forms through the small intestine," *Gut* 27(8):886–892 (1986).

DiSario, J.A. et al., "Sulindac Induces Regression and Prevents Progression of Sporadic Colorectal Adenomas," *Gastroenterology* 112(suppl):A555 (Apr. 1997).

DuBois, R.N. et al., "Nonsteroidal Anti–Inflammatory Drugs, Eicosanoids, and Colorectal Cancer Prevention," *Gastroenterology Clinics of North America* 25(4):773–791 (Dec. 1996).

Duggan, D.E. et al., "The disposition of sulindac," *Clin. Pharm. Therapeutics* 21(3):326–335 (1977).

Fenoglio, C.M. and R.R. Pascal, "Colorectal Adenomas and Cancer," *Cancer* 50(11):2601–2608 (1982).

Gazzaniga, A. et al., "Oral colon–specific drug delivery: design strategies," *S.T.P. Pharma Pratiques* 4(5):336–343 (1994).

Giardiello, F.M. et al., "Treatment of Colonic and Rectal Adenomas with Sulindac in Familial Adenomatous Polyposis," *New England J. Med.* 328(18):1313–1316 (1993).

Gowan, G., "Complete Regression of Villous Adenomas of the Colon Using Piroxacam, a Nonsteroidal Anti–Inflammatory Drug," *Dis. Colon Rectum* 39(1):101–102 (Jan. 1996).

Hanif, R. et al., "Effects of Nonsteroidal Anti–Inflammatory Drugs on Proliferation and on Induction of Apoptosis in Colon Cancer Cells by a Prostaglandin–Independent Pathway," *Biochem. Pharm.* 52(2):237–245 (Jul. 1996).

Hixson, L.J. et al., "NSAID Effect on Sporadic Colon Polyps," *Am. J. Gastroenterology* 88(10):1652–1656 (1993).

Kelloff, G.J. et al., "Clinical development plan: sulindac," *J. Cell Biochem. Suppl* 20:240–251 (1994).

Kerr, J.F.R. et al., "Apoptosis: A Basic Biological Phenomenon with Wide–Ranging Implications in Tissue Kinetics," *Br. J. Cancer* 26(4):239–257 (1972).

Knutson, C.O. and M.H. Max, "Diagnostic and Therapeutic Colonoscopy," *Arch. Surg.* 114(4):430–435 (1979).

Konishi, F. and B.C. Morson, "Pathology of colorectal adenomas: a colonoscopic survey," *J. Clin. Path.* 35(8):830–841 (1982).

Kwan, K.C. and D.E. Duggan, "Pharmacokinetics of Sulindac," *Acta Rhum. Belgica* 1:168–178 (1977).

Labayle, D. et al., "Sulindac Causes Regression of Rectal Polyps in Familial Adenomatous Polyposis," *Gastroenterology* 101(3):635–639 (1991).

Ladenheim, J. et al., "Effect of Sulindac on Sporadic Colonic Polyps," *Gastroenterology* 108(4):1083–1087 (1995).

Lee, F.D., "Importance of apoptosis in the histopathology of drug related lesions in the large intestine," *J. Clin. Path.* 46(2):118–122 (1993).

Lee, S.H. et al., "Selective Expression of Mitogen–inducible Cyclooxygenase in Macrophages Stimulated with Lipopolysaccharide," *J. Biol. Chem.* 267(36):25934–25938 (1992).

Leserman, L.D. et al., "Cell–specific drug transfer from liposomes bearing monoclonal antibodies," *Nature* 293(5829):226–228 (1981).

Levine, D.S. et al., "Coating of Oral Beclomethasone Dipropionate Capsules with Cellulose Acetate Phthalate Enhances Delivery of Topically Active Antiinflammatory Drug to the Terminal Ileum," *Gastroenterology* 92(4):1037–1044 (1987).

Lockshin, R.A. and C. M. Williams, "Programmed Cell Death–I. Cytology of Degeneration in the Intersegmental Muscles of the Pernyi Silkmoth," *J. Insect Physiol.* 11(2):123–133 (1965).

Logan, R.F.A. et al., "Effect of aspirin and non–steroidal anti–inflammatory drugs on colorectal adenomas: case–control study of subjects participating in the Nottingham faecal occult blood screening programme," *Br. Med. J.* 307(6899):285–289 (1993).

Masferrer, J.L. et al., "Endogenous glucocorticoids regulate an inducible cyclooxygenase enzyme," *Proc. Natl. Acad. Sci. USA* 89(9):3917–3921 (1992).

Maskens, A.P., "Histogenesis of Adenomatous Polyps in the Human Large Intestine," *Gastroenterology* 77(6):1245–1251 (1979).

Meade, E.A. et al., "Differential Inhibition of Prostaglandin Endoperoxide Synthase (Cyclooxygenase) Isozymes by Aspirin and Other Non–steroidal Anti–inflammatory Drugs," *J. Biol. Chem.* 268(9):6610–6614 (1993).

Mitchell, J.A. et al., "Selectivity of nonsteroidal antiinflammatory drugs as inhibitors of constitutive and inducible cyclooxygenase," *Proc. Natl. Acad. Sci. USA* 90(24):11693–11697 (1994).

Miyamoto, T. et al., "Purification of Prostaglandin Endoperoxide Synthetase from Bovine Vesicular Gland Microsomes," *J. Biol. Chem.* 251(9):2629–2636 (1976).

Moorghen, M. et al., "A Protective Effect of Sulindac Against Chemically–Induced Primary Colonic Tumours in Mice," *J. Path.* 156(4):341–347 (1988).

Morson, B.C., "Evolution of Cancer of the Colon and Rectum," *Cancer* 34(3):845–849 (1974).

Nakada, I. et al., "Prednisolone therapy for intra–abdominal desmoid tumors in a patient with familial adenomatous polyposis," *J. Gastroenterology* 32(2):255–259 (Apr. 1997).

Neugut, A.I. et al., "The Effect of Calcium and Vitamin Supplements on the Incidence and Recurrence of Colorectal Adenomatous Polyps," *Cancer* 78(4):723–728 (Aug. 1996).

Northway, M.G. et al., "Piroxicam Decreases Postirradiation Colonic Neoplasia in the Rat," *Cancer* 66(11):2300–2305 (1990).

Oshima, M. et al., "Suppression of Intestinal Polyposis in $Apc^{\Delta 716}$ Knockout Mice by Inhibition of Cyclooxygenase 2 (COX–2)," *Cell* 87(5):803–809 (Nov. 1996).

Papahadjopoulos, D. and A. Portis, "Calcium–Induced Lipid Phase Transitions and Membrane Fusion," *Annals NY Acad. Sci.* 308:50–66 (1978).

Pasricha, P.J. et al., "The Effects of Sulindac on Colorectal Proliferation and Apoptosis in Familial Adenomatous Polyposis," *Gastroenterology* 109(3):994–998 (1995).

Peleg, I.I. et al., "Aspirin and nonsteroidal Anti–inflammatory Drug Use and the Risk of Subsequent Colorectal Cancer," *Arch. Internal Med.* 154(4):394–399 (1994).

Piazza, G.A. et al., "Antineoplastic Drugs Sulindac Sulfide and Sulfone Inhibit Cell Growth by Inducing Apoptosis," *Cancer Res.* 55(14):3110–3116 (1995).

Piazza, G.A. et al., "Selective Apoptosis of Neoplastic Cells Accompanies Polyp Regression in Familial Adenomatous Polyposis (FAP) Patients Treated with FGN–1 (Sulindac Sulfone): Evidence for a Cyclooxygenase Independent Mechanism," *Gastroenterology* 112(4 Suppl):A638 (Apr. 1997).

Pritchard, D.M. and A.J.M. Watson, "Apoptosis and Gastrointestinal Pharmacology," *Pharmacol. Ther.* 72(2):149–169 (Nov. 1996).

Rankin, G.B., "Indications, Contraindications, and Complications of Colonoscopy," in: *Gastroenterologic Endoscopy*, Sivak, M.V., ed., W.B. Saunders Co., Philadelphia, publ., pp. 868–880 (1987).

Rao, C.V. et al., "Chemoprevention of Colon Carcinogenesis by Dietary Administration of Piroxicam, α–Difluoromethylornithine, 16α–Fluro–5–androsten–17–one, and Ellagic Acid Individually and in Combination," *Cancer Res.* 51(17):4528–4534 (1991).

Reddy, B.S. et al., "Dose–related Inhibition of Colon–Carcinogenesis by Dietary Piroxicam, a Nonsteroidal Antiinflammatory Drug, during Different Stages of Rat Colon Tumor Development," *Cancer Res* 47(20):5340–5346 (1987).

Reddy, B.S. et al., "Chemoprevention of Colon Carcinogenesis by Concurrent Administration of Piroxicam, a Nonsteroidal Antiinflammatory Drug with D,L–α–Difluromethylornithine, an Ornithine Decarboxylase Inhibitor, in Diet," *Cancer Res.* 50(9):2562–2568 (1990).

Reddy, B.S. et al., "Inhibition of colon carcinogenesis by prostaglandin synthesis inhibitors and related compounds," *Carcinogenesis* 13(6):1019–1023 (1992).

Reddy, B.S. et al., "Inhibitory effect of aspirin on azoxymethane–induced colon carcinogenesis in F344 rats," *Carcinogenesis* 14(8):1493–1497 (1993).

Rex, D.K. et al., "Colonoscopic Miss Rates of Adenomas Determined by Back–to–Back Colonoscopies," *Gastroenterology* 112(1):24–28 (Jan. 1997).

Rex, D.K. et al., "Relative Sensitivity of Colonoscopy and Barium Enema for Detection of Colorectal Cancer in Clinical Practice," *Gastroenterology* 112(1):17–23 (Jan. 1997).

Riendeau, D. et al., "Comparison of the cyclooxygenase–1 inhibitory properties of nonsteroidal anti–inflammatory drugs (NSAIDS) and selective COX–2 inhibitors, using sensitive microsomal and platelet assays," *Can. J. Physiol. Pharmacol.* 75(9):1088–1095 (Sep. 1997).

Rosenberg, L. et al., "A Hypothesis: Nonsteroidal Anti–Inflammatory Drugs Reduce the Incidence of Large–Bowel Cancer," *J. Natl. Cancer Institute* 83(5):355–358 (1991).

Saffran, M. et al., "A New Approach to the Oral Administration of Insulin and Other Peptide Drugs," *Science* 233:1081–1084 (1986).

Savill, J., "Apoptosis in disease," *Eur. J. Clin. Invest.* 24(11):715–723 (1994).

Schatzkin, A. et al., "The Polyp Prevention Trial I: Rationale, Design, Recruitment, and Baseline Participant Characteristics," *Cancer Epidemiology, Biomarkers and Prevention* 5(5):375–383 (May 1996).

Shiff, S.J. et al., "Nonsteroidal Antiinflammatory Drugs Inhibit the Proliferation of Colon Adenocarcinoma Cells: Effects on Cell Cycle and Apoptosis," *Exper. Cell Res.* 222(1):179–188 (Jan. 1996).

Schottenfeld, D. and S.J. Winawer, "Large Intestine," in:*Cancer Epidemiology and Prevention*, Schottenfeld, J.D. and J.F. Fraumeni, eds., W.B. Saunders Company, Philadephia, publ., pp. 703–727 (1982).

Schussheim, A. et al., "Sulindac–Induced Regression of Adenomatous Colonic Polyps in a Child with a History of Hepatoblastoma," *J. Pediatric Gastroenterology and Nutrition* 17(4):445–448 (1993).

Simmons, D.L. et al., "Identification of a phorbol ester–repressible v–src–inducible gene," *Proc. Natl. Acad. Sci. USA* 86(4):1178–1182 (1989).

Sinicrope, F.A. et al., "Spontaneous Apoptotic Indices in Human Colon Carcinomas," *Program of the Annual Meeting of the Am. Gastroenterological Association*:A657 (Apr. 1997).

Skinner, S.A. et al., "Sulindac Inhibits the Rate of Growth and Appearance of Colon Tumors in the Rat," *Arch. Surg.* 126(9):1094–1096 (1991).

Strong, H.A. et al., "Sulindac metabolism: The importance of an intact colon," *Clin. Pharm. Therapeutics* 38(4):387–393 (1985).

Suh, O. et al., "Aspirin Use, Cancer, and Polyps of the Large Bowel," *Cancer* 72(4):1171–1177 (1993)

Swanson, B.N. et al., "Sulindac dispostion when given once and twice daily," *Clin. Pharm. Therapeutics* 32(3):397–403 (1982).

Taha, A.S. et al., "Famotidine for the Prevention of Gastric and Duodenal Ulcers Caused by Nonsteroidal Antiinflammatory Drugs," *New England J. Med.* 334(22):1435–1439 (May 1996).

Thompson, C.B., "Apoptosis in the Pathogenesis and Treatment of Disease," *Science* 267:1456–1462 (1995).

Thun, M.J. et al., "Aspirin Use and Reduced Risk of Fatal Colon Cancer," *New England J. Med.* 325(23):1593–1596 (1991).

Tsujii, M. and R.N. DuBois, "Alterations in Cellular Adhesion and Apoptosis in Epithelial Cells Overexpressing Prostaglandin Endoperoxide Synthase 2," *Cell* 83(3):493–501 (1995).

Tsukada, K. et al., "Noncytotoxic Drug Therapy for Intra–Abdominal Desmoid Tumor in Patients with Familial Adenomatous Polyposis," *Dis. Colon Rectum* 35(1):29–33 (1992).

Vane, J.R. and R.M. Botting, "New insights into the mode of action of anti–inflammatory drugs," *Inflamm. Res.* 44(1):1–10 (1995).

van Stolk, R.U. et al., "Phase I Trial of Sulindac Sulfone in Patients with Familial Adenomatous Polyposis (FAP) with Rectal Polyps: Optimal Dose and Safety," *Program of the Annual Meeting of the Am. Gastroenterological Association*:A673 (Apr. 1997).

van Stolk, R.U. et al., "Clinico–Pathologic Correlation of Rectal Adenoma Regression in Patients with Familial Adenomatous Polyposis (FAP) Treated with Sulindac Sulfone in a Phase I/II Trial," *Program of the Annual Meeting of the Am. Gastroenterological Association*:A673 (Apr. 1997).

Waddell, W.R. et al., "Nonsteroid Antiinflammatory Drugs and Tamoxifen for Desmoid Tumors and Carcinoma of the Stomach," *J. Surg. Oncol.* 22(3):197–211 (1983).

Waddell, W.R. et al., "Sulindac for Polyposis of the Colon," *Am. J. Surg.* 157(1):175–179 (1989).

Winawer, S.J. et al., "Colorectal Cancer Screening: Clinical Guidelines and Rationale," *Gastroenterology* 112(2):594–642 (Feb. 1997).

English Language Abstract of WO 97/03659, Derwent World Patents Index (Dialog File 351), WPI Accession No. 97–145197.

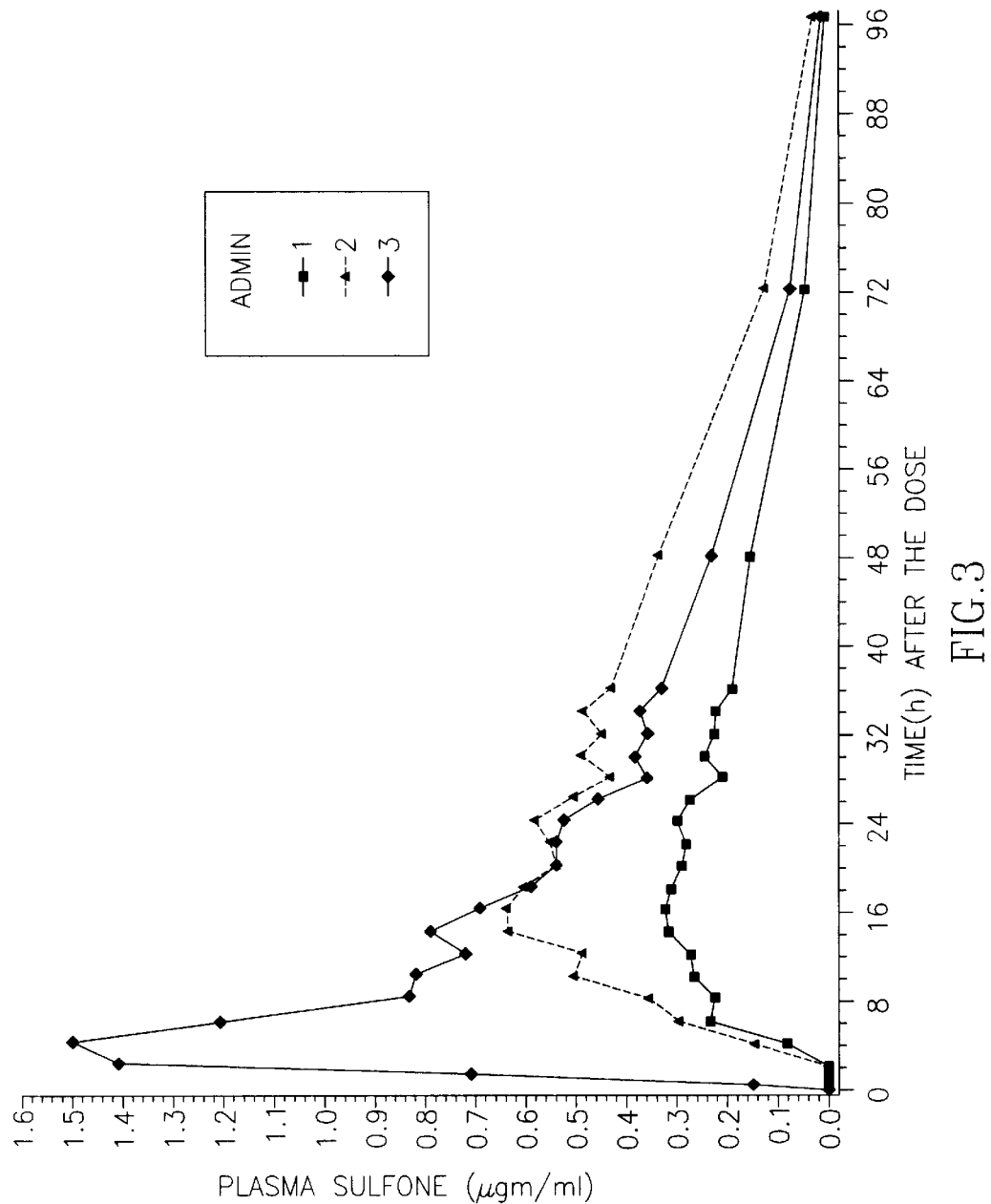

LOCAL DELIVERY OF NON STEROIDAL ANTI INFLAMMATORY DRUGS (NSAIDS) TO THE COLON AS A TREATMENT FOR COLONIC POLYPS

CROSS REFERENCE TO RELATED APPLICATIONS

This application is a continuation in part of U.S. application Ser. No. 08/588,247, filed Jan. 18, 1996, now U.S. Pat. No. 5,840,332 which is incorporated herein by reference.

FIELD OF THE INVENTION

The invention is in the field of polyp and colon cancer chemoprevention and chemotherapy.

BACKGROUND OF THE INVENTION

Colorectal Polyps: The Disease, Diagnosis and Treatment

A colorectal polyp is a circumscribed mass of tissue that projects above the surface of the bowel mucosa. It is classified as pedunculated or sessile, depending on whether it contains a discrete stalk. While most small polyps are asymptomatic lesions detected only by screening or diagnostic studies, larger polyps, greater than 10 mm, may ulcerate and cause intestinal bleeding, as well as have malignant potential.

Colorectal polyps are extremely common in adults in Western countries, they are found in more than 30% of autopsies conducted on people greater than 60 years of age (Correa P., *Gastroenterology* 77:1245–1251 (1979)). The colonic polyp has been implicated as a precursor in the development of colorectal cancer (Morson B. C., *Cancer* 34:845–850 (1974)). Current data suggest a polyp to cancer sequence, with colorectal neoplasmic changes as a continuous process from normal mucosa, to adenoma, and then to carcinoma (Schottenfeld, D. & Winawer, S. J., *Cancer: Epidemiology and Prevention*, Philadelphia, W. B. Saunders, 703–727 (1982)).

Histologically, polyps are classified as neoplastic, i.e., adenomas, with malignant potential or as non-neoplastic, known as benign adenomas (Fenoglio, C. M. & Pascal, R. R., *Cancer* 50:2601–2608 (1982)). Approximately 70% of polyps removed at colonoscopy are adenomas, (Konishi, F. & Morson, B. C., *J. Clin. Pathol.* 35:830–841 (1982)) with the potential to become larger than 10 mm, and therefore, having the probability of becoming tumorigenic. It is, therefore, of great importance to identify colonic polyps and to treat them before they can become malignant.

Most commonly, polyps are described as sporadic, arising spontaneously in about a quarter of the population by age 50, with the prevalence increasing with age, and which may or may not result in colorectal cancer (Winawer, S. J., et al., *Gatstroenterology* 112:594–642 (1997)). Familial adenomatous polyposis (FAP), on the other hand, is an autosomal dominant, inherited disorder, characterized by the presence of hundreds of adenomatous polyps in young adults and in the eventual development of colorectal cancer (Schussheim, A., et al., *Gastroenterol. Nutr.* 17:445–448 (1993)).

Colonoscopy is considered the best method for detecting polyps accurately, especially those measuring less than 10 mm in diameter (Rex, D. K., et al., *Gastroenterology* 112:17–23 (1997)). Most polyps found during colonoscopy can be completely and safely removed by electrocautery (fulguration) (Knutson, C. D. & Max, M. H., *Arch Surg* 114:30–435 (1979)). Some complications, however, may develop during colonoscopy, most commonly perforation and bleeding, occurring in 0.1 to 0.2% of patients (Rankin, G. B., *Gastrointestinal Endoscopy*, Philadelphia, W. B. Saunders, 875–878 (1987)). In addition, it is not always possible to detect all polyps using colonoscopy because of the anatomy of the colon. In fact, in a recent study, it was shown that a carefully performed complete colonoscopy by an experienced examiner will miss an average of about 24% of polyps that are less than 10 mm in diameter (Rex, D. K., et al., *Gastroenterology* 112:24–28 (1997)).

Non-Steroidal Anti-Inflammatory Drugs and Colorectal Polyps

To overcome the current technical limitations of colonoscopy, and to avoid the need for surgical procedures, extensive research has been focused during the past decade on finding pharmacologic agents that might be used to treat or prevent colorectal polyps. Especially, the effect of non-steroidal inflammatory drugs (NSAIDs) on colorectal polyps has become of interest.

Epidemiological studies have shown that chronic aspirin use is associated with a 50–70 percent reduction in the incidence of colorectal cancer (Logan, R. F. A., et al., *Br. Med. J.* 307:285–289 (1993); Rosenberg, L., et al., *J. Natl. Cancer Inst.* 83:355–358 (1991); Thun, M. J., et al., *New Engl. J. Med.* 325:1593–1596 (1991); Suh, O., et al., *Cancer* 72:11171–1177(1993); Peleg II et al., *Arch. Intern. Med.* 154:394–399 (1994)). In addition, multiple animal studies have documented a chemoprotective effect of selected NSAIDs as judged by a reduction in the frequency and number of premalignant and malignant lesions (Reddy, B. S., et al., *Cancer Res.* 50:2562–2568 (1990); Reddy, B. S., et al., *Carcinogenesis* 14:1493–1497 (1993); Rao, C. V., et al., *Cancer Res.* 51:4528–4534 (1991); Craven, P. A., & DeRuberis, F. R., *Carcinogenesis* 14:541–546 (1992); Northway, M. G., et al., *Cancer* 66:2300–2305 (1990); Moorghen, M., et al., *J. Pathol* 156:341–347 (1988); Reddy, B. S., et al., *Cancer Res.* 47:5340–5346 (1987); Reddy, B. S., et al., *Carcinogenesis* 13:1019–1023 (1992); Skinner, S. A., et al., *Arch. Surg.* 126:1094–1096 (1991)). In a recent case study of a patient with villous adenomas of the cecum, who refused surgical resection, a course of NSAID therapy, using piroxicam, 30 mg weekly, showed dramatic and sustained regression of the premalignant adenomas for up to 20 months (Gowen, G. F., *Dis. Colon Rectum* 39:101–102 (1996)). In clinical studies of familial adenomatous polyposis, using the NSAID, sulindac, at a daily dose of 300 mg, taken systemically, it was shown that the number and size of colonic polyps was significantly decreased (Giardelio, F. M., et al., *New Engl. J. Med.* 328:1313–1316 (1993); Labaylle, D., et al., *Gastroenterology* 101:635–639 (1991); Waddell, W. R., et al., *Am. J. Surg.* 157:175–179 (1989)). In a small pilot study, in which sulindac or piroxicam was used against sporadic colonic polyps, however, there was no similar regression of adenomatous polyps (Ladenheim, J., et al., *Gastroenterology* 108:1083–1087 (1995); Hixson, L. J., et al., *Am. J. Gastroenterol* 88:1652–1656 (1993)). These results, however, were disputed in a more recent multicenter study of nearly 100 patients, with sporadic polyps of 4–12 mm. When sulindac, 300 mg daily, or sulindac, 150 mg daily, or placebo, were given for one year, it was demonstrated that sulindac, regardless of dose, induced regressions and prevented the progression of sporadic colorectal adenomas (DiSario, J. A., et al., *Gastroenterology* 112 (Suppl):555A (1997)).

NSAIDs and Apoptosis

The precise mechanism responsible for the anti-neoplastic effect of NSAIDs is unknown. A number of recent publications have suggested that NSAIDs may be accomplishing these chemoprotective effects by induction of apoptosis, the "programmed cell death" phenomenon (Savill, J., *Eur. J. Clin. Invest.* 24:715–723 (1994); Thompson, C. B., *Science* 267:1456–1462 (1995); Bright, J. and Khar, A., *Biosci Rep.* 14:67–81 (1994)). In 1965, Lockshin and colleagues introduced the concept of "programmed cell death" to describe the phenomenon that had long been observed in embryogenesis where certain predetermined cells in the embryo would die at a particular stage during development (Lockshin, R. A. and Williams, C. M. *J. Insect Physiol.* 11:123–133 (1965)). In 1972, Kerr et al., linked this concept with a mode of cell death, defined on strict morphological criteria such as the detachment of a cell from its substratum, coupled by the fragmentation of the nucleus and cytoplasm, in a process which, they termed "apoptosis." (Kerr, J. F. R., et al., *Br. J Cancer* 26:239–257 (1972)). This active cell death, under tight genetic control, is found in all tissues, and is responsible both for regulating cell number and type, as well as for disposing cells with damaged or mutant DNA. Defects in apoptosis, however, can lead to cancer, autoimmune disease and neurodegeneration (Pritchard, D. and Watson, A. J. M., *Pharmacol Ther.* 72:149–169 (1996)).

Defective apoptosis has been implicated in the pathogenesis of colorectal cancer. In 1995, Bedi et al. quantified the amount of apoptosis in frozen sections of biopsies of colorectal epithelium from normal mucosa, adenomas from patients with familial adenomatous polyposis, sporadic adenomas, and carcinomas by in situ nick end labeling of histopathological specimens cultured for up to 24 hours on plastic. There was progressive inhibition of apoptosis during the transformation of normal epithelium into carcinomas (Bedi, A., et al.,*Cancer Res.* 55:1811–1816 (1995)).

Additionally, other studies support the contention that NSAIDs may exert their effect on colorectal polyps and carcinoma by inducing apoptosis. Pasricha et al. investigated the rate of proliferation and apoptosis in the flat colorectal mucosa of patients with familial adenomatous polyposis after treatment with sulindac. No effects on proliferation were found, but the sulindac-treated group showed increased levels of colonic mucosal apoptosis (Pasricha, P. J., et al., *Gastroenterology*, 109:994–999 (1995)). Piazza et al. similarly demonstrated the induction of apoptosis in an HT-29 colon adenocarcinoma cell line following sulindac administration, but found no evidence of cell proliferation or differentiation (Piazza, R., et al., *Cancer Res.* 55:3110–3116 (1995)). In a clinical study, Lee found that there were increased levels of apoptotic bodies in colonic biopsies from patients with diclofenac-induced colitis (Lee, F. D., *J Clin Pathol* 46:18–122 (1993)).

Induction of Apoptosis via COX-2

The mechanism whereby an NSAID induces apoptosis may be attributed to its known inhibition of cyclooxygenase-2 (COX-2), an enzyme associated with the inflammatory process (Vane, J. R. and Botting, F. M., *Inflamm. Res.* 44:1–10 (1995)). Prostaglandins are synthesized by the cyclooxygenase enzyme, of which there are two known isoforms, COX-1 (Miyamoto, T., et al., *J. Biol. Chem.* 251:2629–2636 (1976)) and COX-2 (Simmons, D. I., et al., *Proc. Natl. Acad. Sci. USA* 86:1178–1182 (1989)). COX-1 is a constitutive enzyme expressed in many tissues including the gastric mucosa, whereas COX-2 is an inducible enzyme expressed in fibroblasts, macrophages and other cell types in inflammation (Masferrer, J. L., et al.,*Proc. Natl. Acad. Sci. USA* 89:3917–3921 (1992); Lee, S. K., et al., *J. Biol. Chem.* 267:25934–25938 (1992)). Although NSAIDs can inhibit both COX isoforms, they are selective in their inhibition rates of these enzymes. Diclofenac sodium and piroxicam, for example, exert a strong inhibitory effect on COX-2, (Meade, E. A., et al.,*J. Biol. Chem.* 268:6610–6614 (1993)) while sulindac mainly exerts an inhibitory effect on COX-1. It has been suggested that the GI side effects associated with NSAIDs relate to COX-1 inhibition, while the anti-inflammatory effects of NSAIDs, relate to COX-2 inhibition (Mitchell, J. A., et al., *Proc. Natl. Acad. Sci. USA* 90:11693–11697 (1994)).

The induction of apoptosis as a result of COX-2 inhibition by NSAIDs has been implicated in the observed effects of NSAIDs on colonic polyp regression. This possible relationship between COX-2 inhibition by NSAIDs and apoptosis was demonstrated in a study by Tsujii and DuBois (Tsujii, M. and DuBois, R. N., *Cell* 83:493–501 (1995)). They transfected a rat intestinal epithelial cell line with mRNA for COX-2, thereby inducing COX-2 overexpression, and showed that these cells showed increased adhesion to the extracellular matrix and became resistant to butyrate-induced apoptosis. The authors proposed that COX-2 over-expression enhances the induction of tumors by changes in cellular adhesion and apoptosis inhibition.

There is considerable evidence for the association of an inhibition of COX-2 activity or expression with polyp and/or tumor regression. It has been observed that the disruption of the COX-2 gene reduces the number of tumors in mice by more than six-fold. Additional treatment of these mice with drugs that selectively inhibit the COX-2 enzyme results in a marked reduction of tumor multiplicity (Oshirna, K., et al., *Cell.* 87:803–809 (1996)). COX-2 expression is elevated in intestinal tumors which develop in carcinogen-treated rats. Treatment of these animals with many different NSAIDs results in a marked decrease in tumor multiplicity (DuBois, R. N., et al., *Gastroenterology Clinics of North America* 25:773–391 (1996)). Taking all these results together, it appears likely that COX-2 may be involved in the adenoma to carcinoma sequence, and that both highly potent and selective COX-2 inhibitors (such as diclofenac sodium), and weak inhibitors of COX-2 (such as sulindac) may be effective in polyp regression in both FAP and in sporadic polyps.

Although sulindac is only a weak inhibitor of COX-2, sulindac itself may not be the active agent in these studies. Sulindac has two metabolites that are formed following extensive first pass metabolism. One metabolite, sulindac sulfone, is formed via an irreversible oxidation. The second metabolite, sulindac sulfide, is formed via a reversible reduction. These two metabolites are considered to be more active than the sulindac itself (Brogden, R. N. et al., *Drugs* 16:97–114 (1978)).

For example, the anti-inflammatory activity that is associated with sulindac is primarily attributed to the more active metabolite, sulindac sulfide (Kwan, K. C. et al., *Acta Rheumatol. Belg.* 1:168–178 (1977)). Sulindac sulfide is a potent inhibitor of COX-2 (Riendeau E. et al., *Can. J. Physiol. Pharmacol.* 75:1088–1095 (1997)). Sulindac sulfide has also been found to be effective against several biochemical markers for colon cancer. It has been demonstrated that sulindac sulfide is six times more potent than sulindac in reducing proliferation and inhibiting the cell cycle in HT-29 colon adenocarcinoma cells (Schiff, S. J. et al., *Exp. Cell Res.* 222:179–188 (1996)) and that sulindac sulfide induced cell cycle inhibition in SW480 colon carcinoma cells (Lemoine, M. et al., *Gastroenterology* 112 (*suppl.*): A673 (1997)). The other metabolite, sulindac sulfone, is relatively inactive and does not show any anti-inflammatory activity (Kelloff et al.,*J. Cell Biochem.* 20 (*suppl.*): 240–251 (1994)) but has shown some anti-neoplastic activity (Piazza, G. A. et al., *Gastroenterology* 112 (*suppl.*): A638 (1977)).

The association of NSAIDs with polyp and/or tumor regression is clear. The evidence for COX-2 involvement is very strong; however, in addition, other mechanisms may also play a role.

Local Delivery of NSAIDs to the Colon

A disadvantage of most NSAID therapy for colorectal polyps is that the NSAID is given systemically, and for long periods. Prolonged high systemic concentrations of many NSAIDs can result in other complications unrelated to the polyp treatment. For example, such NSAID users have a three-fold greater risk of developing serious GI complications over non-NSAID users. It has been estimated that 20% to 40% of patients on systemic NSAID therapy develop peptic ulcers (Taha, A., et al., N. Engl. J. Med. 334:1435–1439 (1996)). It has also been estimated that 10,000–20,000 fatalities a year occur in the United States from NSAID-induced gastrointestinal disorders. Other adverse effects of NSAIDs include renal failure, hepatic dysfunction, bleeding and gastric ulceration. The side effects of NSAIDs are especially of concern in the elderly, the very population most at risk for the development of colonic polyps. Therefore, a need exists for an alternative method to target therapeutic concentrations of NSAIDs to the site of colonic polyps.

Sulindac, given orally as a tablet, is primarily absorbed through the gastrointestinal tract. The peak plasma concentration is reached about two hours after dosing (Swanson, B. N. et al., Clin. Pharmacol. Ther. 32:397–403 (1982)). As a result of sulindac's extensive first-pass metabolism to its active metabolites, the plasma concentrations of sulindac sulfide and sulindac sulfone will exceed the levels of sulindac within four hours after dosing. Thereafter, these metabolites will remain the two major components in the blood while the concentration of sulindac will rapidly taper off (Duggan, D. E. et al., Clin. Pharmacol. Ther. 21:326–335 (1977)).

It has been demonstrated that although sulindac that is administered orally is primarily absorbed into the blood, a certain amount reaches the colon. The sulindac that reaches the colon will be reduced by the colonic microflora exclusively to sulindac sulfide, resulting in a high lumenal concentration of sulindac sulfide in the colon (Hanif, R. et al., Biochem. Pharmacol. 52:237–245 (1996)). The sulindac sulfide that is formed will then be absorbed through the colon walls to the bloodstream. This premise is supported by the fact that sulindac sulfide appears in the plasma long after sulindac and sulindac sulfone have been excreted in the urine and feces and that these findings are not seen in patients who underwent a colectomy and ileostomy (Strong, H. A. et al., Clin. Pharmacol. Ther. 38:387–393 (1985)). It can be concluded that the intact colon plays a significant role in the sustained presence of sulindac sulfide in the blood and that deliverying the entire dose of the sulindac to the colon will result in a significant enhancement of the formation of sulindac sulfide over the less active metabolite, the sulindac sulfone.

Local Delivery of Drugs to the Colon

U.S. Pat. No. 5,498,608 (Johnson, L. K.) describes the use of 2-hydroxy-5-phenylazobenzoic acid derivatives for the treatment of colon cancer. The derivatives are prodrugs that are converted into an active antiinflammatory drug by the action of colonic bacteria. The use of these agents for the treatment or prevention of colon cancer is proposed.

U.S. Pat. No. 5,686,589, U.S. Pat. No. 5,401,774, U.S. Pat. No. 5,643,959, EP 485,171, EP 485,173, and EP 508,586 (Brendel, K.) describes conjugating drugs into a prodrug form with substituted fused ring phenylacetic acids as a mechanism to deliver the active agent, such as an NSAID, to a colonic polyp. Colonic bacterial enzymes then cleave the active agent from the macromolecule.

U.S. Pat. No. 5,686,105 and U.S. Pat. No. 5,686,106 (both to Kelm, G. R.) describe the use of polymers to coat an active agent for delivery to the colon. The polymers dissolve at about the time that the dosage form reaches the inlet between the small intestine and the colon, or thereafter in the colon. Examples of such polymers include Eudragit® L and cellulose acetate phthalate. Examples of the types of agents that can be provided to the colon in this manner include agents for the topical treatment of diseases of the colon, such as irritable bowel syndrome, Crohn's disease, ulcerative colitis and carcinomas. Examples of the specific active agents that are listed include nonsteroidal antiinflammatory drugs, and chemotherapeutics for treatment of carcinomas.

U.S. Pat. No. 5,464,633 (Conte, U., et al.) describes a tablet that consists of a core containing the active substance, and an external layer that is able to prevent the immediate release of the active substance. The external layer can be a natural and/or synthetic polymeric substance in the class of the erodible and/or gellable and/or soluble in an aqueous medium hydrophilic polymers and adjuvant substances. Lastly, the layer is surrounded by a gastroresistant and enterosoluble coating.

SUMMARY OF THE INVENTION

Recognizing the need for treating colonic polyps in a manner that results in a minimal number of systemic side effects, and cognizant of the problem of delivering efficacious levels of drugs to the colonic environment, the inventors investigated methods by which therapeutic levels of drugs might be presented to the colonic environment.

These studies cumulated in the discovery of a method of administering sulindac to a patient in need of same, which method enhances the amount of sulindac which is converted into the more active metabolite, sulindac sulfide, in such patient, when compared to the amount that is converted into sulindac's less active metabolite, sulindac sulfone, in the same patient, by minimizing the amount of sulindac that is absorbed into the bloodstream and by maximizing the amount of sulindac that is delivered to the colon—at which location the sulindac is preferentially metabolized into sulindac sulfide by the colonic environment and absorbed therefrom.

These studies also cumulated in the discovery of a novel composition or formulation for the oral administration of a colonic delivery system (CDS), and method for use of the same, for providing a desired agent to the colon of human and animal patients in need of the same.

Thus, in a first embodiment, a method is provided for the administration of sulindac to a patient in need of the same wherein the most if not all of the dose of sulindac that is administered to such patient is delivered to the colon of the patient.

In a further embodiment, a composition or formulation designed for oral administration of a colonic delivery system (CDS) is provided, such formulation containing the structure of a coated core in which the core contains a desired agent. The coat of the coated core is based on a formulation that comprises water insoluble hydrophilic particulate matter embedded in a water-insoluble carrier; the formulation is such that when exposed to an aqueous environment, the particulate matter in the coat absorbs water, thus forming channels that interconnect the inner core with the outer surface of the coating. These channels allow aqueous solutions to enter the core and drug to diffuse out.

In a further embodiment, the invention is directed to a method of administering the compositions as above, wherein the most or all of the dose of a desired agent is delivered to the colon. In a preferred embodiment, the colonic contents or cell walls metabolize the drug to a more desired form, for example, a more active metabolite, such more desired form thus being synthesized in a preferential manner and locally higher concentration by such delivery directly to the colon than when the drug is administered systemically or orally in a conventional manner.

In a further embodiment, the invention is directed to compositions and the administration of the same as above, wherein the drug is an NSAID.

In a further embodiment, the invention is directed to compositions and the administration of the same as above, wherein the more active metabolite is a COX-2 inhibitor.

In a further embodiment, the invention is directed to compositions and administration of the same as above, wherein the drug and metabolite are sulindac and sulindac sulfide, respectively.

In a further embodiment, the invention is directed to compositions and administration of the same as above, especially NSAID and most especially sulindac, for the treatment and prevention of polyps or cancer, especially colonic cancer.

BRIEF DESCRIPTION OF THE DRAWINGS

FIG. 3 shows the averaged data for the concentration of sulindac sulfone in the blood in the three treatments listed in the legend to FIG. 1.

DETAILED DESCRIPTION OF THE PREFERRED EMBODIMENTS

Definitions

Figure 1:
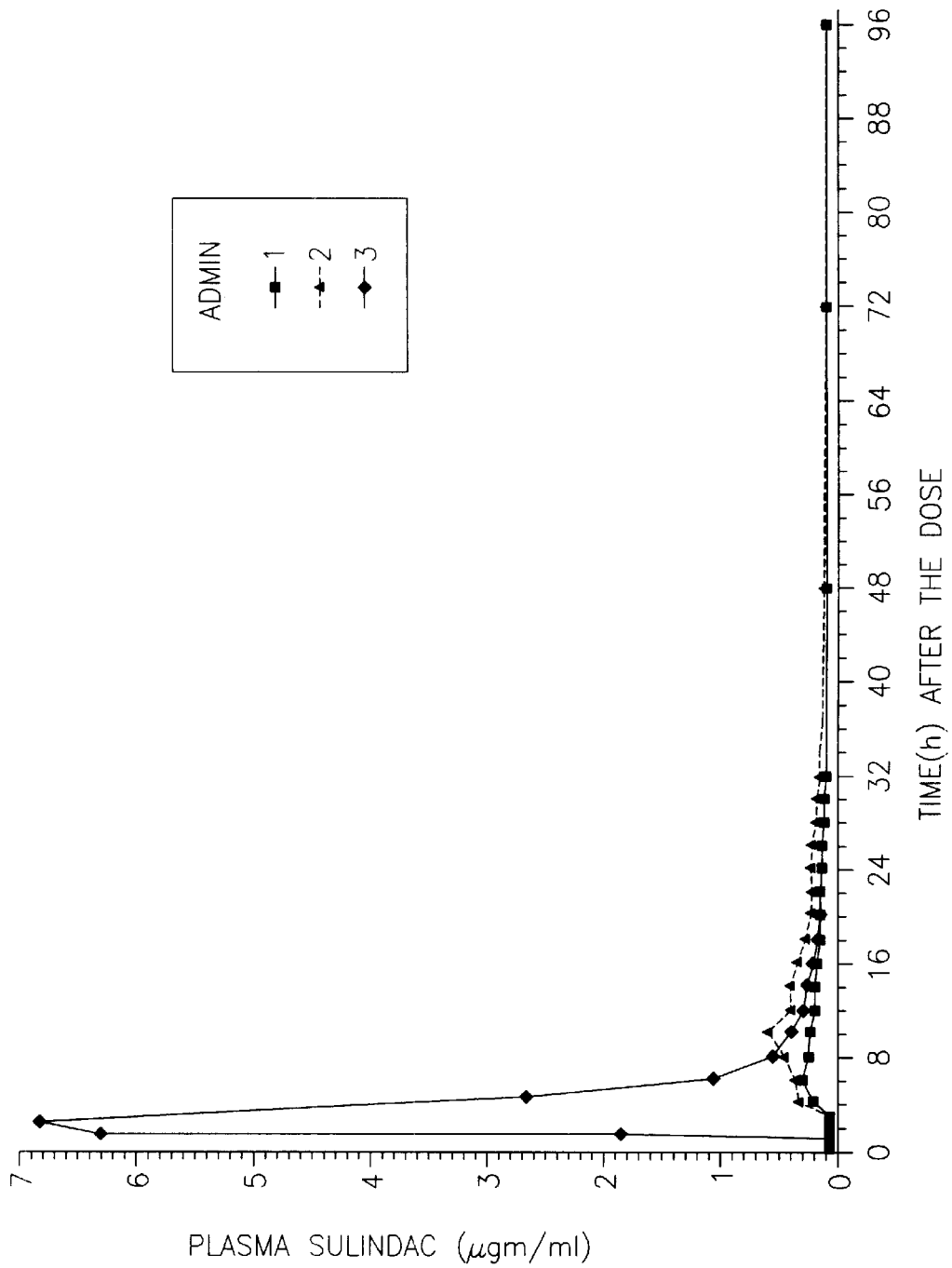
FIG. 1 shows the averaged data for sulindac in three different treatments: Treatment A: One tablet sulindac CDS; Treatment B: Two tablets of sulindac CDS; and Treatment C: Two tablets of commercial sulindac

In the description that follows, a number of terms used in pharmacology are extensively utilized. In order to provide a clear and consistent understanding of the specification and claims, and the scope to be given such terms, the following definitions are provided.

By the term "colon" is meant that part of the large intestine that extends from the cecum to the rectum. The cecum is the blind pouch in which the large intestine begins and into which the ileum opens from one side.

By the term "matrix" is meant a surrounding substance within which something else is contained. In a preferred embodiment, the matrix is a material comprising a natural polymer that can be modified or unmodified, but that, in its unmodified form, is resistant to enzymatic degradation in the stomach and small intestine by pancreatic enzymes. Preferably the matrix is a natural polymer that is not enzymatically degraded in the stomach, for example, a calcium pectinate-pectin polymer which is preferentially degraded in the colon, as opposed to the stomach and small intestine.

By the term "NSAID" is meant a Non-Steroidal Anti-Inflammatory Drug; that is, any drug classified as having non-steroidal antiinflammatory properties. An NSAID acts by impairing prostaglandin synthesis. The term "NSAID" is intended to be interpreted broadly and is not limited in terms of chemical composition.

By the term "treat" as in "treat a patient," is meant to give medical aid to such patient, especially, for the purposes of preventing the development of, or preventing the worsening of an undesired physiological or medical condition, or for the purposes of ameliorating such condition in such patient, either human or animal. Unless otherwise stated, the term "treat" is not limited to any particular length of time or to any particular level of dose.

By the term "more active metabolite" is meant a metabolite of a drug that gives enhanced desired clinical effect in comparison to the effect that is achieved by the unmetabolized drug.

By the term "precancerous lesion" is meant a lesion that exhibits histologic changes that are associated with an increased risk of cancer development. Examples include adenomatous polyps of the colon. Certain syndromes that commonly display precancerous lesions are also referred to by the term "precancerous" including dysplastic nevus syndrome and the colonic polyposis syndromes. The term "precancerous lesions" refers to such lesions or syndromes whether or not the lesions are clinically identifiable.

By the term "sensitive to treatment" is meant that a target that it is desired to treat (for example, the cells of a precancerous or cancerous lesion) directly or indirectly respond in a beneficial manner to the influence of an agent, especially, an agent that has an antiproliferative effect on such cells. "High risk" polyps patients are patients who have had three or more polyps found during a colonoscopic examination.

The invention is directed to a formulation comprising a colonic delivery system and a desired agent such as a drug, and methods for using the same. In a preferred embodiment, such agent is susceptible to a metabolism in the colon and colonic metabolism results in the formation of either different metabolites or in different amounts of various metabolites than would have been formed when compared to the type and/or amount of such metabolite that are formed when the drug is allowed to be absorbed into the bloodstream prior to reaching the colon. According to the invention such colonic metabolism preferentially forms a greater percentage or larger amounts of a desired active metabolite of the drug than would be formed by allowing the drug to be absorbed into the bloodstream. Thus, by delivering the drug directly to the colon, a greater percentage of the total dose of the drug is converted into such desired active metabolite than would have been converted had the drug been allowed to be absorbed into the bloodstream prior to reaching the colon. Local colonic natural production of more active metabolites, which may be achieved by colonic natural flora, or via metabolic routes, will further enhance the desired clinical effect and allow the achievement of colonic drug levels of these metabolites that are unattainable by systemic or conventional oral delivery.

In a preferred embodiment, the drug is sulindac, the desired metabolite is sulindac sulfide, and the undesired metabolite is sulindac sulfone. The sulindac can be provided alone or in combination with other therapeutic agents and at doses and times known in the art. The sulindac can be administered to the patient in a dose of 2–500 mg daily for 1–12 months in single or divided doses. In another embodiment, the dose of sulindac that is administered to the patient is 2–500 mg daily chronically in single or divided doses. Preferred doses are 50–500 mg/day in single or divided doses, most preferably 150–300 mg/day in single or divided doses. Any delivery system that will deliver the sulindac to the colon can be used. Sulindac delivered directly to the colon is converted into the active metabolite sulindac sulfide, which, in addition to creating a relatively high local colonic concentration of sulindac sulfide, can be absorbed into the bloodstream from the colon. Sulindac delivered preferentially to the colon will result in highly significant concentrations of the potent COX-2 inhibitor metabolite in the lumenal contents of the colon and in the colon wall, allowing anti-inflammatory and anti-neoplastic activity not otherwise attainable at the lower concentrations formed through systemic delivery. Use of this method results in an enhanced concentration of sulindac sulfide and in a more efficacious treatment for the prevention or regression of colon polyps and for the prevention or treatment of colon cancer. The device of the invention can be coated with an enteric coating. Sulindac that is in a tablet or capsule of the invention can be released in a burst or in a controlled fashion. The sulindac can also be encapsulated in a microsphere, a liposome, a nanosphere or a microemulsion, or be provided in the form of pellets or minitablets.

In addition to sulindac, other orally administered drugs or chemical agents that are processed to active metabolites by the colonic environment can be administered to a patient in need of the same in a similar manner. Especially, other orally administered drugs or agents that are preferentially metabolized in the colon to metabolites that are different than, and/or present in different amounts than, the metabolites that are formed when an orally administered drug is allowed to be absorbed into the bloodstream prior to reaching the colon. Examples of such drugs include drugs that are susceptible to the formation of sulfide and sulfone metabolites, similar to sulindac, or other drugs or chemical agents that have active metabolites formed by reductive processes.

In a further embodiment, orally administered drugs or chemical agents that are processed to active metabolites in the colonic environment can be administered to a patient who suffers from impaired liver function. This impaired function impairs normal hepatic metabolism of drugs to active metabolites. Metabolism in the colon can serve an alternative for metabolism in the liver for such drugs in these patients.

In a further embodiment, the methods of the invention are used to deliver an NSAID locally to the colon of a patient in need of the same, so that such NSAID can exert its effects directly on the colon. Such method obviates concerns about systemic overdosing of the NSAID. In addition, such method allows a study of the mechanism of action of the NSAID since it provides a mechanism of assessing the local effects of the drug.

In a preferred embodiment, the sulindac or desired drug or agent is administered to a patient in need of the same using a colonic delivery system that is the subject of U.S. Pat. Nos. 5,525,634 and 5,840,332 and U.S. application Ser. No. 08/969,796, each incorporated herein by reference. The colonic delivery system of the invention is preferably one that comprises a core and a coating. Preferably, the coat is based on a formulation that comprises water-insoluble hydrophilic particulate matter embedded in a water-insoluble carrier, such that when exposed to an aqueous environment, the particulate matter absorbs water, thus forming channels that interconnect the core with the outer surface of the coating, thus providing channels for aqueous solutions to enter the core and for the drug to diffuse out. The colonic delivery systems described above serve as a means to target enterally administered drugs to the large intestine. When the drug-matrix composition of the invention is present in the stomach or the small intestine, its drug content is shielded by the coating and is not significantly released until arrival in the colon. Release in the colon gives significantly higher concentration of drug at the site of action than systemic delivery and metabolism to more active moieties results in concentrations of these active agents unattainable by other means.

Accordingly, a subject in need of treatment with a desired drug, especially when it is desired to target the desired drug to the site of such subject's colon, may conveniently obtain such treatment by orally ingesting the composition of the invention. Alternatively, if desired, the composition of the invention may be provided in suppository form. Compositions for rectal administration are preferably suppositories which may contain, in addition to the active substance, excipients such as cocoa butter or a suppository wax. The composition of the invention may also be administered directly into the colon of such patient by the physician at the time of colonoscopy, Subjects in need of treatment according to the method of the invention are especially those who are at risk for development of polyps and/or colon cancer and most especially high risk patients as previously defined. Types of polyp conditions or syndromes that would benefit by treatment according to the invention include adenomatous colonic polyps (especially of the large bowel, the precursor lesions for the vast majority of colorectal cancers), common sporadic polyps, familial adenomatous polyposis (FAP), polyposis syndromes, Gardner's Syndrome with colon polyposis, and colorectal carcinoma. The difference between common sporadic polyps and polyposis syndromes is dramatic. Common sporadic polyp cases are characterized by relatively few polyps, each of which can usually be removed leaving the colon intact. By contrast, polyposis syndrome cases can be characterized by many (hundreds or more) of polyps literally covering the colon in some cases, making safe removal of the polyps impossible short of surgical removal of the colon.

Thus, according to the invention, colon polyps or colon cancer can be treated or prevented in a patient in need of the same by administering one or more NSAIDs to the patient in a composition or device that minimizes release of at least one of the NSAIDs prior to at least that NSAID reaching the patient's colon, and that maximizes release of at least that NSAID in the patient's colon.

Examples of NSAIDs that may be provided in the composition, delivery system and methods of the invention include, for example, the carboxylic acid NSAIDs and the pyrazolone butazone propazone NSAIDs. Examples of the carboxylic acid NSAIDs include such as anthranilic acids, aspirin(5-acetylsalicylic acid), azodisal sodium, carbohet-erocyclic acids, carprofen, chlorambucil, diclophenac, fenbufen, fenclofenac, fenoprofen, flufenamic acid, flurbiprofen, fluprofen, furosemide, gold sodium thiomalate, ibuprofen, indomethacin, indoprofen, ketoprofen, lonazolac, loxoprofen, meclofenamic acid, mefanamic acid, melphalan, naproxen, penicillamin, phenylacetic acids, proprionic acids, salicylic acids, salazosulfapyridine, sulindac, sulindac sulfide, sulindac sulfone, and tolmetin. Examples of the pyrazolone butazone propazone NSAIDs include meloxicam, oxicams, piroxicam (for example, feldene or piroxicam beta cyclodextran), and tenoxicam. Other NSAIDs useful in the practice of the invention include etodolac and oxaprozin. Other suitable embodiments useful in the practice of the invention are combinations of an NSAID with other agents, for example, as provided by Arthrotec (a combination of diclofenac sodium and misoprostol, a synthetic prostaglandin, Searle). Combinations of non-steroid (NSAID) anti-inflammatory drugs such as sodium diclofenac, sulindac, endomethycin, ibuprofen, ketoprofen, diflunisal piroxicam, naproxicam, naproxen, flurbiprofen, sodium tolmetin, any other agent having NSAID activity, drugs of peptidic nature and cyclooxygenase inhibitors may be present in the composition of the present invention.

Therapeutic agents suitable for incorporation into dosage forms of the present invention are those for which release in the colon or delayed release is therapeutically advantageous. These include therapeutic agents useful for topical treatment of diseases of the colon such as polyps, carcinomas, and infection in which systemic absorption of a therapeutic agent is neither required nor desired. These include non-steroidal anti-inflammatory drugs such as 5-amino salicylic acid, immunosuppressants such as cyclosporine A, and chemotherapeutics such as methotrexate for treatment of carcinomas.

In another embodiment, chemotherapeutic agents are administered contemporaneously with an enzyme cyclooxygenase inhibitor. Examples of inhibitors include nonsteroidal anti-inflammatory drugs (NSAID), wherein the addition of an enzyme cyclooxygenase inhibitor to the treatment enhances the antitumor effects of the chemotherapeutic agent by blocking metabolism of arachidonic acid to inhibit cell regulation processes. Examples of inhibitors include nonsteroidal anti-inflammatory drugs such as minocycline hydrochloride (Nino), Diflunisal (Diflun) or Sulindac (Sulin). The NSAID can be a COX-2 specific inhibitor or a COX-1 specific inhibitor.

In a preferred embodiment, one method to avoid gastropathy problems that occur with NSAIDs is the combination of the NSAID, where possible, with a gastric mucosal barrier protector such as the prostoglandin E2 agonist, misoprostol. Other NSAIDs that are especially useful in the practice of the invention include those that selectively inhibit COX-2 more than they do COX-1. Meloxicam is a first generation NSAID which is selective COX-2 inhibitor and relatively more gastric friendly. Another NSAID useful in the practice of the invention is nabumetone. Another medication useful in the practice of the invention is acetaminophen. In another embodiment, at least one of the drugs is a COX-1 specific inhibitor.

A wide variety of chemotherapeutic drugs may be employed individually or in combination. The drugs may be embedded in, or bound to, the matrix. Binding may be through complexation, salt formation, coordination complexes or the like. The drugs may be used individually or in combination depending upon the nature of the drug, the tumor and whether cooperative action is pharmacologically indicated. The drug composition can be provided in a form that is modified, for example. In a preferred embodiment, a drug is modified to provide for bonds that allow enzymatic cleavage, for example, by hydrolysis.

In a preferred embodiment of this invention, the drug that is incorporated is one which undergoes metabolism to a more active metabolite. This metabolite is preferentially formed in the colon as compared to levels of this metabolite that are formed as a result of hepatic metabolism or small bowel wall metabolism that occur when the drug is allowed to be absorbed into the bloodstream. The therapeutic benefits of the colonic delivery system depend upon its ability to directly deliver efficacious levels of agents such as the desired NSAIDs to the colon. This allows the local treatment of colonic diseases, such as colonic polyps and colon carcinoma. Direct delivery of drugs to the colon enhances the amount of drug absorbed in the colon, and the amount of drug to which colon cells are directly exposed. Direct delivery or targeting of drugs also decreases the systemic distribution of the drugs, thereby reducing undesirable and potentially harmful side effects. Direct delivery of such drugs to the large intestine can considerably decrease the required effective dose.

In the controlled-release systems currently known in the art, drugs are released by diffusion mechanisms during transit of the drug-containing composition throughout the gastrointestinal tract. The drug is absorbed and metabolized in the gut wall or in the liver. Only a small portion of the drug reaches the colon and that portion is in a diluted state having been diluted by intestinal fluids. Less of the drug is available for treatment and less is available for the advantageous metabolism to a more active moiety. According to the present invention this problem is overcome by incorporating the drug in a suitable colonic delivery matrix or, if the drug is contained in a core, coating such core with a suitable coating that can deliver the drug preferentially to the colon. Examples of such matrices and coatings are found in the patents and patent applications U.S. Pat. Nos. 5,525,634 and 5,840,332 and U.S. application Ser. No. 08/969,796, each incorporated herein by reference. Thus, in such systems, most if not the entire dose of the drug is delivered to the colon for treatment of the colon polyps, and most or the entire dose is available for advantageous metabolism to a highly active species.

In a preferred embodiment a modified pectin is used for the matrix. The pectin is modified to reduce its solubility (hydrophilicity), at acidic gastric pHs and at neutral intestinal pHs. A pectin of low methoxy content (i.e. degree of esterification <40%) is reacted with a divalent metal salt, preferable calcium chloride, in an alcohol:water mixture. The alcohol is most preferably either ethanol or isopropyl alcohol. Other cations, such as magnesium, strontium, aluminum, and iron salts can replace the calcium in modifying the pectin for use in the matrix formulation of the drug.

In a highly preferred embodiment, the drug is formulated with calcium pectinate, low methoxy pectin and hydroxypropylmethylcellulose in suitable amounts. The calcium pectinate can range from 20% to 40%, the pectin from 10% to 30%, the hydroxypropylmethylcellulose from 10% to 35% and the drug from 0.5% to 50%. In a most highly preferred example of this embodiment, the percentages are calcium pectinate 22%, low methoxy pectin 22%, hydroxypropylmethylcellulose 13% and sulindac 43%. The tablets further contain magnesium stearate and may be coated with a standard enteric coating based on Eudragit L.

After preparing the pectin matrix, the matrix is combined with a drug. Methods are known for formulating a composition to allow controlled release of the chosen pharmaceutical compound. Using these and other known methods, compositions of the desired pharmaceutical compound may be formulated with the polymers of the present invention. Examples of such methods are disclosed in Saffran et al., *Science* 233:1081–1084 (1986) and Levine et al., *Gastroenterology* 92:1037–1044 (1987).

In an initial study of ten healthy volunteers, in which placebo calcium pectinate matrix tablets were administered, the transit time and disintegration of the radiolabeled formulation was followed by gamma scintigraphy. It was demonstrated that the tablets arrived in the colon essentially intact and that complete tablet disintegration occurred in the colon in all subjects (Adkin, D. A., et al., *Pharmaceutical Research* 14,1:103–107 (1997), incorporated herein by reference.

Specific embodiments of prepared formulations of the compositions of the invention, include, for example, matrix-drug tablets, especially tablets prepared by compression (compressed tablets); matrix-drug pellets, either free or packed in gelatin capsules, or any other means allowing oral administration; matrix-drug nanoparticles, either free or packed in gelatin capsules or any other means allowing oral administration; and multi-layered tablets which comprise cored drug, coated with biodegradable polymers, the polymeric layer being prepared, for example, by spray-coating, molding or double-press procedure. All of these techniques for preparation of such formulations are well known in the art. The tablet or capsule can be coated with an enteric coating.

In a further embodiment of this invention, the drug is incorporated in a core which can be a colonic delivery core as above or a conventional tablet core. The drug can be present in this core at a level of 0.1 to 99%. The core is further coated with a coating suitable for controlled delivery in the gastrointestinal tract as is described in U.S. Pat. No. 5,840,332, incorporated herein by reference. The concentration of particles, the size of the particles and the coating thickness is controlled to effect colonic delivery. In a preferred embodiment, the water-insoluble coating is Eudragit E, the water-insoluble hydrophilic particulate matter is calcium pectinate, the particle size is <150 microns. Eudragit E is a dimethylaminoethylmethacrylate/methylmethacrylate and butylmethacrylate copolymer—a copolymer that is based on neutral methacrylic acid esters and diethylaminoethyl methacrylate esters in which the polymer is cationic in the presence of acids. The particulate matter is preferably present in 50–90% by weight and the coating thickness is preferably between 5 and 150 microns. In a most preferred embodiment, the calcium pectinate is present at 70% by weight and the coating thickness is about 40 microns and the core contains 100 mg sodium diclofenac.

In a most highly preferred embodiment, the drug is preferentially metabolized in the colon to a more active or more selective metabolite. In an example of such a most highly preferred embodiment, 150 mg sulindac is incorporated in a colonic delivery matrix core of 9 mm diameter containing 77.5 mg calcium pectinate, 77.5 mg low methoxy pectin, 45 mg hydropropylmethylcellulose and 1.8 mg magnesium stearate. This core was further coated with 3:7 wgt:wgt Eudragit E:calcium pectinate of particle size <150 microns at a coating thickness of about 35 microns. This system was further coated with a standard enteric coating of Eudragit L. The oral administration of such compositions results in the sulindac being delivered to the colon where it is preferentially metabolized to sulindac sulfide, a more active metabolite with considerable COX-2 activity.

The colonic delivery system of the invention contains the therapeutic agent, alone or in combination with other therapeutic agents, and contains the agents in any dosage level necessary to achieve a therapeutic benefit. The dosage level used depends upon the disease to be treated. Further, the level of one therapeutic agent may be present at a level different from the level of the other therapeutic agents present and each agent may be released at different levels and at different intervals than the other therapeutic agents present. The agent can be adjusted such that it is administered for, for example, a desired length of seconds, minutes, hours, or days that will give the desired therapeutic results. The colonic delivery system of the invention that contains one or more desired therapeutic agents can be administered sporadically only when as needed or for extended periods of time, such as weeks, months or years, as desired to achieve a therapeutically beneficial result.

The actual dosage levels of active ingredients in the compositions of the invention may be varied so as to obtain an amount of active ingredient effective to achieve polyp-eliminating activity in accordance with the desired method of administration. The selected dosage level depends upon the nature of the active compound administered, the route of administration, the desired duration of treatment, and other factors, such as, for example, the age of the patient. If desired, the daily dose may be divided into multiple doses for administration, for example, two, three, or four times a day. The colonic delivery system contains the therapeutic agent, alone or in combination with other therapeutic agents, and may be administered before diagnosis and for diagnostic or prophylactic purposes.

The amount of drug can vary as desired for efficacious delivery of the desired drug and in consideration of the patient's age, sex, physical condition, disease, and other medical criteria. In addition, the amount of drug delivered by the system of the invention will depend upon the relative efficacy of the drug. The amount of specific drug necessary for efficacious results in the delivery system and methods of the invention may be determined according to techniques known in the art. For example, recommended dosages such as known in the art (or example, see the *Physicians' Desk Reference*, 1991 (E. R. Barnhart, publisher), *The Merck Index*, 10th Edition, Merck & Co., New Jersey, and *The Pharmacological Basis of Therapeutics*, 8th edition, A. G. Goodman, et al., eds., Pergamon Press, New York), provide a basis upon which to estimate the amount of a drug which has been previously been required to provide an efficacious level of activity. Especially, amounts of a desired drug that have previously been administered by suppository formulations, and the known characteristics of such drug when administered by suppository, are useful in this regard. Since the delivery system of the invention does not depend upon systemic (blood) delivery of the drug to the colon, it may be expected that efficacious levels of colon drugs that must be administered to a patient systemically will be higher than efficacious levels of such drugs when delivered directly to the colon. Furthermore, it is expected that through colonic delivery, levels of the drug concentration at the site of action, and levels of active metabolites at the site of action will be higher than those attainable through systemic delivery.

It should be noted that the nature, particle size, and weight percentage, of the hydrophilic non-water-soluble particulate matter and the overall coating thickness of the delivery system coating can be varied to fine-tune the delivery to a desired site, or to adjust for a certain physiological condition of the patient. Making the insoluble particles relatively more hydrophilic or increasing their weight percent in the coating, or making their average particle size smaller for a given weight percent or making the coating thinner, all tend to promote a quicker release of the drug from the delivery system. These factors can each be altered and controlled independently of the others. The ratio of the calcium pectinate to the low methoxy pectin can also be optimized to give the best delivery profile in the colon. Increasing calcium pectinate lowers the solubility of the matrix, thus slowing erosion, while increasing pectin gives a stronger gel, thus slowing diffusion of a soluble drug from the matrix.

Tablets and capsules may be prepared and tested by techniques well known in the art, for example, as described in *Remington's Pharmaceutical Sciences*, Mack Publishing Company, 16th edition, 1980, and especially in chapter 89, the pharmaceutical preparation and manufacture of "Tablets, Capsules and Pills." In all embodiments, if desired, more than one drug may be supplied to the patient in the same matrix. Good results have been obtained by the combined administration of for examples, sulindac, tamoxifen and vitamin C; tamoxifen and sulindac; warfarin and vitamin K1; and steroids and tamoxifen. These are cited in the following references: Waddell, W. R., Gerner, R. E., Reich, M. P., *Nonsteroid Anti-inflammatory Drugs and Tamoxifen for Desired Tumors and Carcinoma of the Stomach, J. Surg. Oncol.* 22:197–211 (1983); Tsukada, K., Church, J. M., Jagelman, D. G., et al., *Noncytoxic Drug Therapy for Intra Abdominal Desmoid Tumor in Patients with Familial Adenomatous Polyposis, Dis. Colon Rectum* 35:29–33 (1992). Other chemical substances which may have use in the practice in the invention are vitamin A, vitamin C, vitamin D, vitamin E, multivitamin compositions, calcium and mineral supplementation. Other chemical compounds having use in the practice of the invention are carotenoids, anti-oxidant vitamins, folic acid and flavenoids. In addition, the matrix can be used to release therapeutic levels of dietary supplements such as metals, trace elements, etc., to combat certain conditions including anemia, for example.

After administration into a patient's or an animal's body, the instant tablets or capsules release the therapeutic agent contained therein relatively slowly as the water-soluble carrier absorbs water and forms channels or as the crosslinked substance is slowly biodegraded. The sustained release action may also render it possible to increase the interval between administrations and to reduce the total number of administrations necessary. Furthermore, it is an important advantage of the instant system that the rate of release of active material therefrom may be controlled by incorporating into the tablet or capsule an inactive form of an enzyme capable of dissolving the matrix structure. This inactive form of the enzyme is preferably an enzyme capable of degrading the polysaccharide nature of the matrix. The inactive form of the enzyme is incorporated into the tablets or capsules by simply dispersing it in the matrix with the active substance. The inactive form of the enzyme has no effect upon the microcapsule or tablet structure when stored dried, but when the tablets or capsules are administered into an animal or patient, the inactive form of the enzyme is gradually converted into the active form and the active form of the enzyme attacks the matrix structure present in the tablets or capsules thereby speeding up the release of the active substance therefrom.

In accordance with the present invention, the matrix may be used in microparticles that contain the drug enclosed with them. The microparticles may have a permeable water insoluble matrix selected from proteinaceous materials, polysaccharides, such as pectin, for example, and mixtures thereof. In another aspect of the invention there is also dispersed throughout the matrix a combining agent, such as other polysaccharides or proteinaceous materials, which are capable of absorbing, and adsorbing, substances present in biological fluids.

Microparticles are also useful in chemical reactions in the present invention. For example, microparticles having a water insoluble enzyme matrix can be utilized to catalyze certain chemical reactions. Despite being crosslinked and rendered water insoluble during preparation of the microparticles, the proteinaceous or polysaccharide material, whether present as matrix material or combining agent, retains sufficient activity to absorb substances in biological fluids. Moreover, the microparticles retain their permeability despite being crosslinked. Thus, the particles increase in size, e.g., as well as allowing biological fluids to penetrate them.

Another embodiment of this invention also includes a multi-layer slow release composite. More particularly, in this embodiment, this invention relates to a multi-layered slow release composite wherein layers having a physiologically active substance encapsulated therein alternate with layers having no physiologically active substance encapsulated therein.

Prodrugs, either alone or in combination with other prodrugs or drugs, may be used in the practice of this invention. Many prodrugs have been proposed for specific colonic delivery wherein the active moiety is bound to a sugar or a polymer (carrier molecule) which renders the active molecule inactive. Upon colon arrival, the special chemistry of the colon contents or the colon microflora release the drug from its carrier molecule. Some such prodrugs are partially or significantly absorbed through the GI tract thereby preventing some of the drug from arriving in the colon to be metabolized to the active drug. Even such prodrugs that are not absorbed are diluted by intestinal fluids making the concentration of the obtained metabolite lower than that obtainable by delivering the same prodrug with the delivery systems of this invention. Delivery of the prodrug preferentially to the colon will result in higher concentrations of the active moiety than otherwise attainable. This should be useful for local treatment of disease and to assist in concentration gradient driven drug absorption.

The drug matrix combination of the invention can also be provided in liposomes, or, comprise liposomes. Controlled release liposomal liquid pharmaceutical formulations for injection or oral administration are described in Suzuki et al, U.S. Pat. No. 4,016,100. Liposomal applications for oral drug delivery of lyophilized liposome/peptide drug mixture filled into intestine capsules have also been suggested as in Horokoshi et al., U.S. Pat. No. 4,348,384. As already indicated in some instances the drug will be encapsulated particularly in liposomes. Liposomes are prepared from a variety of lamellar forming lipids including phospholipids, for example, phosphatidyl choline, phosphatidyl ethanolamine, gangliosides and sphingomyelin, steroids and cholesterol. Usually the weight of the lipids in relation to the weight of drug will range from 1 to 5 liters of entrapped drug per mole of amphipathic lipid. In addition the drugs can be employed encapsulated in liposomes or other controlled rate release compositions which are included in the matrix compositions so as to provide for separate and distinct rates of release for the drug. In this way, multiphasic compositions can be prepared so as to provide for sustained release of the drug or drugs over long periods of time. Formation of liposomes with inclusion of various materials is described in Papahadjopoulos (1978) Annals of the N.Y. Academy of Science 308; Gregoriadis and Allison (1980) Liposomes and Biological Systems, John Wiley & Sons; Leserman et al., *Nature* 293:226–228 (1981).

Other suitable embodiments will be known to those of skill in the art. A useful formulation will be suitable for enteric administration, will contain a drug targeted for release in the colon, and will further contain either a saccharide containing polymer matrix and/or a particulate containing coating according to the invention. The formulation will be designed so as to allow protection of the drug from stomach and intestinal enzymes, but permitting release of the drug in the colon either by biodegradation of the matrix or by drug diffusion through the particulate channels in the coating.

The delivery system and methods of the invention are not limited to administration to humans and are especially useful for veterinary administration of drugs to any animal, including pets such as dogs, cats, horses, fish and birds, zoo animals, wild animal control and treatment, and agriculturally important animals of the food and dairy industry such as cattle, milk cows, swine and poultry.

The following examples further describe the materials and methods used in carrying out the invention. The examples are not intended to limit the invention in any manner.

EXAMPLE 1

Cross-Over Pilot Colonic Delivery Study

A cross-over pilot colonic delivery study involving two NSAID (diclofenac sodium) colonic drug delivery tablet formulations with different coating levels and either a commercial slow release (SR) diclofenac sodium or a diclofenac sodium-matrix CDS without a CDS coating as reference was performed in 12 healthy volunteers. The objective of the study was to provide a comparison of the local colonic delivery of two coated sustained release (SR) colonic delivery system (CDS) formulations containing 100 mg sodium diclofenac to a matrix CDS formulation and to a commercial diclofenac slow release formulation (100 mg) as a positive control.

To this end, sodium diclofenac was formulated into a matrix tablet of 9 mm diameter which contained 100 mg diclofenac sodium, 80 mg calcium pectinate, 50 mg low methoxy pectin, 70 mg hydroxypropylmethylcellulose, and 0.6 mg magnesium stearate. This tablet was coated with the CDS particulate-containing coating where the hydrophobic insoluble polymer was Eudragit E and the hydrophilic, water-insoluble particles were calcium pectinate of particle size <150 microns at 70% by weight. Treatment A was coated with about a 35 micron thick CDS coating and subsequently with a standard enteric coating based on Eudragit L. Treatment B was coated with about a 60 micron thick CDS coating and subsequently with a standard enteric coating. Treatment D was not coated with the CDS particulate containing coating but was coated with the same standard enteric coating as the other two treatments. Treatment C was a commercially available slow release diclofenac formulation that made no claims of colonic delivery. It was administered for purposes of comparison.

The trial methodology was an open label, blinded to the analyst, three-way randomized cross-over design (Latin square) with twelve (12) volunteers. The twelve volunteers were divided into two groups. One group received the following three treatments:

A. Diclofenac sodium CDS with 35 micron CDS coating+ enteric coat;
B. Diclofenac sodium CDS with 60 micron CDS coating+ enteric coat;
C. Commercial diclofenac sodium SR tablet.

The second group received the following three treatments:

A. Diclofenac sodium CDS with 35 micron CDS coating+ enteric coat;
B. Diclofenac sodium CDS with 60 micron CDS coating+ enteric coat;
D. Diclofenac sodium CDS+enteric coat.

Each volunteer received one of the treatments at baseline and the others with a washout phase of at least one week between the drug administrations. Venous blood samples were taken before dosing and at predetermined intervals between 4 and 36 hours after dosing. The concentration of diclofenac was determined in the blood samples using a validated procedure based on extraction and HPLC analysis. Colonic delivery is shown by the time profile of diclofenac in the blood. Adverse effects were monitored at each visit.

Pharmacokinetic Results

The plasma concentration curves of diclofenac showed more than one peak in several instances. $C_{max}$ and $t_{max}$ relate to the highest observed concentration regardless of other peaks present in the graph. The $t_{max}$ of the averaged data for Treatments A and B was 12 hours and 16 hours respectively. Table 1 collects the individual data for $C_{max}$ and $t_{max}$ for the twelve volunteers.

TABLE 1

Individual Data for $C_{max}$ and $t_{max}$

| Treatment | $C_{max}$ (ng/ml) A | $t_{max}$ (hours) A | $C_{max}$ (ng/ml) B | $t_{max}$ (hours) B | $C_{max}$ (ng/ml) C | $t_{max}$ (hours) C | $C_{max}$ (ng/ml) D | $t_{max}$ (hours) D |
|---|---|---|---|---|---|---|---|---|
| volunteer | | | | | | | | |
| 1 | 144 | 16 | 192 | 28 | 395 | 6 | | |
| 2 | 245 | 12 | 228 | 14 | 123 | 6 | | |
| 3 | 321 | 12 | 328 | 14 | 573 | 4 | | |
| 4 | 179 | 18 | 105 | 14 | 222 | 6 | | |
| 5 | 232 | 8 | 257 | 18 | 223 | 6 | | |
| 6 | 213 | 14 | 170 | 20 | | | | |
| 7 | | | 96 | 36 | | | | |
| 8 | 426 | 12 | 452 | 12 | | | 151 | 16 |
| 9 | 482 | 14 | | | | | | |
| 10 | 226 | 16 | 416 | 16 | | | 290 | 10 |
| 11 | 176 | 18 | 274 | 24 | | | 186 | 18 |
| 12 | 383 | 16 | 277 | 24 | | | 212 | 22 |
| Mean | 275.2 | 14.2 | 254.1 | 20.0 | 307.2 | 5.6 | 209.8 | 16.5 |
| STDDEV | 111.6 | 3.0 | 114.3 | 7.4 | 177.9 | 0.9 | 59.1 | 5.0 |
| Median | 232 | 14 | 257 | 18 | 223 | 6 | 199 | 17 |
| Maximum | 482 | 18 | 452 | 36 | 573 | 6 | 290 | 22 |
| Minimum | 144 | 8 | 96 | 12 | 123 | 4 | 151 | 10 |

The mean $t_{max}$±Standard Deviation for the individual data for Treatments A and B was 14.2±3.0 hours (n=11) and 20.0±7.4 hours (n=11) with ranges (maximum–minimum) of 18–8 hours and 36–12 hours respectively. The variability in $t_{max}$ was greater for Treatment B than for Treatment A, indicating a possible dependence of the variability on the value of $t_{max}$. The positive control, Treatment C, delivered its maximum concentration at an earlier time. The $t_{max}$ for the averaged data was six hours and the mean $t_{max}$ for the individual data was 5.6±0.9 hours (n=5) with the data ranging from 6–4 hours. The mean $t_{max}$ for the individual data for Treatment D was 16.5±5.0 hours (n=4) with a range 22–10 hours. The $t_{max}$ data clearly shows a delayed delivery of the Diclofenac from Treatments A and B as compared to Treatment C. Treatment D shows both early and delayed drug delivery.

The mean $C_{max}$ for Treatment A was 275.2±111.6 ng/ml (n=11) with the values ranging from 482–144 ng/ml, for Treatment B the values were 254.1±114.3 ng/ml (n=11) with the values ranging from 452–96 ng/ml, for Treatment C the mean $C_{max}$ was 307.2±177.9 (n=5) with the values ranging from 573–123 ng/ml, and for Treatment D the mean $C_{max}$ was 209.8±59.1 ng/ml (n=4) with a data range of 290–151 mg/ml. All three CDS formulations had lower mean maximal concentrations than the commercial SR formulation.

The results of the extent of absorption to six hours ($AUC_{0-6}/AUC_{0-36}$) for the individual profiles are collected in Table 2. AUC is the area under the curve for the concentration versus time graph. $AUC_{0-36}$ is the area under the curve for the entire measurement period of 36 hours and represents the full extent of drug absorption. $AUC_{0-6}$ represents the area under the same curve from zero to six hours and represents the diclofenac sodium found in the blood in the first six hours. The quotient of these numbers represents the fraction of the drug absorbed that is absorbed in the first six hours. One can see that the mean value for treatments A and B are 0.08±0.03 and 0.05±0.05 with ranges of 0.16–0.03 and 0.13–0.00 respectively while for Treatment C the mean value is 0.59±0.13 with a range of 0.69–0.37. Treatment D gave a mean value of 0.22±0.09 with a range of values of 0.33–012. The extent of absorption to six hours is clearly much lower for Treatments A and B, of intermediate nature for Treatment D and is high for Treatment C.

TABLE 2

Extent of Absorption to Six Hours
Summary for $AUC_{0-6}/AUC_{0-36}$

| Treatment vol# | A | B | C | D |
|---|---|---|---|---|
| 1 | 0.08 | 0.06 | 0.37 | |
| 2 | 0.16 | 0.11 | 0.66 | |
| 3 | 0.05 | 0.00 | 0.61 | |
| 4 | 0.07 | 0.00 | 0.64 | |
| 5 | 0.10 | 0.06 | 0.69 | |
| 6 | 0.09 | 0.00 | | |
| 7 | | 0.13 | | |
| 8 | 0.08 | 0.08 | | 0.12 |
| 9 | 0.06 | | | |
| 10 | 0.10 | 0.05 | | 0.33 |
| 11 | 0.06 | 0.00 | | 0.20 |
| 12 | 0.03 | 0.02 | | 0.22 |
| Mean | 0.08 | 0.05 | 0.59 | 0.22 |
| STDDEV | 0.034 | 0.047 | 0.129 | 0.087 |
| MAX | 0.16 | 0.13 | 0.69 | 0.33 |
| MIN | 0.03 | 0.00 | 0.37 | 0.12 |

The results for the calculation of the $AUC_{0-36}$ for the individual data for all the volunteers are collected in Table 3.

TABLE 3

Summary of Individual AUC Data

| | PPL#1 | PPL#2 | Commercial SR | PPL-UC |
|---|---|---|---|---|
| | | Treatment | | |
| | A | B | C | D |
| | | volunteer | | |
| | $AUC_{0-36}$ (h)(ng/ml) | $AUC_{0-36}$ (h)(ng/ml) | $AUC_{0-36}$ (h)(ng/ml) | $AUC_{0-36}$ (h)(ng/ml) |
| 1 | 1828 | 1418 | 1060 | |
| 2 | 1760 | 1360 | 707 | |
| 3 | 2878 | 2696 | 3526 | |
| 4 | 1682 | 1395 | 1031 | |
| 5 | 1822 | 1682 | 1082 | |
| 6 | 1821 | 1592 | | |
| 7 | | 1043 | | |
| 8 | 2578 | 2126 | | 1757 |
| 9 | 2421 | | | |
| 10 | 2737 | 2361 | | 2639 |
| 11 | 2294 | 2563 | | 2518 |
| 12 | 2329 | 2552 | | 2576 |
| Mean | 2192.7 | 1889.8 | 1481.2 | 2372.5 |
| STDDEV | 427.8 | 584.5 | 1153.3 | 413.3 |
| Median | 2294 | 1682 | 1060 | 2547 |
| Maximum | 2878 | 2696 | 3526 | 2639 |
| Minimum | 1682 | 1043 | 707 | 1757 |

The mean $AUC_{0-36}$ for the individual data for Treatments A, B, C and D were 2193±428, 1890±585, 1481±1153 and 2373±413 (h)(ng/ml) showing that the CDS formulations were better than, or at least as good as, the positive control in this respect. The value for the positive control might be artificially low because a two hour time point was not taken. There is no difference seen between the $AUC_{0-36}$ values for the three CDS formulations. The values for the $AUC_{0-36}$ for the averaged values are identical to the average values for the individual data.

Diclofenac was quantifiable (defined as a mean concentration above the lowest quantifiable concentration of the analysis—10 ng/liter) for Treatment A from 4 hours to 30 hours, for Treatment B from 4 hours to 36 hours, for Treatment D from 4 hours to 30 hours while for Treatment C from 4 hours to 12 hours. The individual data for the number of quantifiable results for each formulation as a function of time are collected in Table 4.

TABLE 4

| Time (hours) | Treatment A Q/T[1] | Treatment B Q/T[1] | Treatment C Q/T[1] | Treatment D Q/T[1] |
|---|---|---|---|---|
| 0 | 0/11 | 0/11 | 0/5 | 0/4 |
| 4 | 10/11 | 6/11 | 4/5 | 4/4 |
| 6 | 11/11 | 7/11 | 5/5 | 4/4 |
| 8 | 11/11 | 8/11 | 5/5 | 4/4 |
| 10 | 11/11 | 7/11 | 5/5 | 4/4 |
| 12 | 11/11 | 9/11 | 4/5 | 4/4 |
| 14 | 11/11 | 8/11 | 1/5 | 4/4 |
| 16 | 11/11 | 8/11 | 1/5 | 4/4 |
| 18 | 11/11 | 8/11 | 1/5 | 4/4 |
| 20 | 10/11 | 11/11 | 1/5 | 3/4 |
| 22 | 11/11 | 11/11 | 1/5 | 3/4 |
| 24 | 11/11 | 10/11 | 1/5 | 4/4 |
| 26 | 10/11 | 8/11 | 1/5 | 4/4 |
| 28 | 7/11 | 9/11 | 0/5 | 2/4 |
| 30 | 7/11 | 8/11 | 0/5 | 2/4 |
| 36 | 4/11 | 7/11 | 0/5 | 1/4 |

[1]Q/T is number quantifiable/total number of measurements.

The individual data corroborate that the CDS formulations give quantifiable concentrations of diclofenac for times that the formulation is expected to be in the colon, compared to Treatment C which was quantifiable up to only 12 hours in four of the five volunteers.

Discussion

The coated CDS formulations, Treatments A and B, showed their maximal concentrations at times that clearly correspond to colonic drug absorption. The residence time in the stomach for the fasted state is up to two hours and the average transit time in the small intestine is 3–5 hours (Davis, S., et al., Gut 27:886 (1986)) so that a $t_{max}$ greater than six hours is indicative of colonic absorption. The values of 14 hours for the coated CDS Treatment A, 20 hours for the coated CDS Treatment B, and 16 hours for the non coated CDS Treatment D, are indicative of the maximal drug delivery taking place in the colon. The positive control, Treatment C, delivered its maximum concentration at a time that corresponds to small intestinal delivery.

The area under the concentration versus time curve to a given time represents the amount of the drug absorbed up to that time point. The ratio of that area to the total area gives a representation of the percentage of the total drug absorbed that was absorbed up to that point. The percent extent of absorption in the first six hours (defined as (100) ($AUC_{0-6}$/$AUC_{0-36}$) where $AUC_{0-6}$ is the area under the concentration vs. time curve from 0 to 6 hours and $AUC_{0-36}$ is the area under the entire curve in our experiment) from the averaged data was 8% for Treatment A, 4% for Treatment B, 59% for Treatment C and 23% for Treatment D indicating essentially colonic delivery for Treatments A and B, mostly colonic delivery for treatment D and mostly small intestine delivery for Treatment C.

These values again clearly indicate that Treatments A and B deliver the drug essentially in the colon while Treatment C delivers the majority of its drug before colonic arrival. The non-coated CDS, while delivering it maximal drug concentration through the colon, delivered some of the drug before arrival in the colon.

Blood $C_{max}$ levels were lower for the colonic delivery formulations than for the commercial SR product. It is expected that colonic delivery thus promotes a lower incidence of systemically caused side effects.

Safety Evaluation

Twelve subjects were evaluated for safety. No serious adverse events occurred in the course of the study. Seven subjects showed mild adverse events, not all of which are drug related.

Conclusions

The new colonic delivery systems resulted in diclofenac concentrations that were quantifiable for 24 to 28 hours, indicating sustained colonic delivery of the drug. The CDS with the coatings gave low drug release in the first six hours, indicating effective protection of a soluble drug before colonic arrival. It is therefore concluded that the CDS is an effective and well tolerated NSAID drug delivery system to the large intestine.

EXAMPLE 2

A Pharmacokinetic Study of Sulindac and Its Metabolites

A crossover pharmacokinetic study involving two dosing levels of CDS-sulindac with one dose of commercially available sulindac as a reference was performed. The objective of the study was to compare the pharmacokinetic profile of sulindac delivered to the colon to sulindac delivered to the upper GI tract (stomach and small intestine) and to compare the concentrations and relative formation of the two major metabolites of sulindac, sulindac sulfide and sulindac sulfone.

To this end sulindac was formulated into a CDS 9 mm tablet containing 150 mg sulindac, 77.5 mg calcium pectinate, 77.5 mg low methoxy pectin, 45 mg hydroxypropylmethylcellulose, and 1.8 mg magnesium stearate. This tablet was coated with about a 30 micron thick CDS coating consisting of 30% Eudragit E and 70% calcium pectinate of particle size <150 micron and further coated with an enteric coat based on Eudragit L. Commercially available 150 mg tablets of sulindac were used as a reference material.

The trial methodology was an open label, blinded to the analyst, three-way crossover design with 18 volunteers. Each of the volunteers received all three treatments in random order, one at baseline and the other two at intervals of one week for drug washout. The three treatments were:

A. One tablet sulindac CDS

B. Two tablets of sulindac CDS

C. Two tablets of commercial sulindac

Venous blood samples were taken before dosing and at predetermined time intervals from 0.5 to 96 hours after dosing. The concentration of sulindac was determined in the blood samples using a validated sample preparation procedure and an HPLC analysis. The concentrations of sulindac and its metabolites sulindac sulfide and sulindac sulfone were monitored. Colonic delivery is shown by the time profile of sulindac in the blood. Differences between the hepatic metabolism of sulindac in the blood and colonic metabolism of sulindac are evaluated by monitoring the concentrations of the metabolites and the parent drug as a function of time.

Results—sulindac

The concentration profiles of sulindac in plasma for the two CDS treatments were similar but quite different from that of the commercial sulindac. $C_{max}$ and $t_{max}$ relate to the highest observed concentration. The averaged data for sulindac in all three treatments are shown in FIG. 1. The $t_{max}$ of the averaged data for treatments A and B was 6 hours and 10 hours respectively. The $t_{max}$ for the averaged data for treatment C was 3 hours. The individual data for $t_{max}$ and $C_{max}$ for the 18 volunteers is provided in Table 5. The mean $t_{max}$±standard deviation for the three treatments was 8.3±5.5, 7.00±2.80, and 1.66±0.86 hours respectively with ranges (maximum–minimum) of 28–4, 12–4, and 4–0.5 hours respectively. When compared to treatment C, the two CDS tablets showed delayed delivery of the sulindac.

TABLE 5

$C_{max}$ and $t_{max}$ for Sulindac

| Volunteer No. | Treatment A | | Treatment B | | Treatment C | |
|---|---|---|---|---|---|---|
| | $C_{max}$ (µg/ml) | $t_{max}$ (hours) | $C_{max}$ (µg/ml) | $t_{max}$ (hours) | $C_{max}$ (µg/ml) | $t_{max}$ (hours) |
| 1 | 0.26 | 8 | 0.77 | 10 | 6.26 | 2 |
| 2 | 0.43 | 6 | 2.70 | 10 | 5.77 | 1 |
| 3 | 0.17 | 10 | 0.24 | 4 | 7.46 | 1 |
| 4 | 0.14 | 6 | 0.45 | 6 | 8.75 | 1 |
| 5 | 0.25 | 10 | 0.45 | 12 | 8.24 | 2 |
| 6 | | | | | 9.59 | 2 |
| 7 | 0.07 | 6 | 0.2 | 4 | 4.57 | 2 |
| 8 | 0.85 | 6 | 1.15 | 4 | 9.75 | 2 |
| 9 | 0.11 | 4 | 0.18 | 10 | 5.35 | 1 |
| 10 | 0.14 | 4 | 0.48 | 8 | 9.76 | 2 |
| 11 | 0.53 | 8 | 0.36 | 8 | 3.77 | 4 |
| 12 | 0.18 | 6 | 0.38 | 4 | 6.57 | 0.5 |
| 13 | | | | | | |
| 14 | 0.24 | 28 | 1.0 | 8 | 9.08 | 2 |

TABLE 5-continued $C_{max}$ and $t_{max}$ for Sulindac

| Volunteer No. | Treatment A $C_{max}$ (μg/ml) | Treatment A $t_{max}$ (hours) | Treatment B $C_{max}$ (μg/ml) | Treatment B $t_{max}$ (hours) | Treatment C $C_{max}$ (μg/ml) | Treatment C $t_{max}$ (hours) |
|---|---|---|---|---|---|---|
| 15 | | | | | 9.52 | 1 |
| 16 | 0.23 | 10 | 1.09 | 8 | 8.07 | 2 |
| 17 | | | | | 9.70 | 1 |
| 18 | 0.17 | 6 | 0.66 | 4 | 9.53 | 4 |
| Mean | 0.27 | 8.3 | 0.72 | 7 | 7.75 | 1.7 |
| Standard | 0.21 | 5.5 | 0.65 | 2.8 | 1.99 | 0.8 |
| Maximum | 0.85 | 28 | 2.70 | 12 | 9.76 | 4 |
| Minimum | 0.07 | 4 | 0.18 | 4 | 3.77 | 0.5 |

The mean $C_{max}$ for treatment A was 0.27±0.21 (μg/ml) with the values ranging from 0.85–0.07, for treatment B was 0.72±0.65 (μg/ml) with the values ranging from 2.7–0.18, while for treatment C the value was 7.76±1.99 (μg/ml) with the values ranging from 9.76–3.77. The $C_{max}$ of sulindac was considerably lower for the CDS formulations.

The area under the curve of concentration of sulindac vs. time (AUC) for all 18 volunteers is given in Table 6. The mean AUC from zero to 96 hours ($AUC_{0-96}$) was 3.50±2.50 (h)(μg/ml) with values ranging from 8.63 to 0.24 for treatment A, 8.42±6.37 (h)(μg/ml) with values ranging from 22.8 to 2.48 for treatment B and 25.66±7.52 (h)(μg/ml) with values ranging from 43.57 to 13.2. The AUC for the sulindac from the CDS formulations were considerably lower than the commercial product.

TABLE 6

$AUC_{0-96}$ for Sulindac

| Volunteer No. | Treatment A $AUC_{0-96}$ (h)(μg/ml) | Treatment B $AUC_{0-96}$ (h)(μg/ml) | Treatment C $AUC_{0-96}$ (h)(μg/ml) |
|---|---|---|---|
| 1 | 2.88 | 5.7 | 19.26 |
| 2 | 3.86 | 21.26 | 22.38 |
| 3 | 2.17 | 4.72 | 26.56 |
| 4 | 3.26 | 5.76 | 18.55 |
| 5 | 2.52 | 2.46 | 26.94 |
| 6 | | | 34.21 |
| 7 | 0.24 | 2.98 | 13.20 |
| 8 | 7.68 | 12.88 | 36.32 |
| 9 | 2.96 | 5.81 | 22.16 |
| 10 | 0.46 | 5.36 | 33.00 |
| 11 | 4.62 | 4.97 | 16.41 |
| 12 | 3.61 | 5.89 | 19.73 |
| 13 | | | |
| 14 | 8.85 | 22.80 | |
| 15 | | | 30.05 |
| 16 | 3.76 | 10.61 | 24.54 |
| 17 | | | 39.43 |
| 18 | 3.73 | 5.71 | 27.99 |
| Mean | 3.61 | 8.35 | 25.61 |
| Standard | 2.3 | 6.37 | 7.52 |
| Maximum | 8.85 | 22.80 | 39.43 |
| Minimum | 0.24 | 2.46 | 13.20 |

TABLE 7

Extent of Absorption of Sulindac at Six Hours

| | Total Absorption $AUC_{0-96}$ | To 6 Hours $AUC_{0-6}$ | Extent of Absorption $AUC_{0-6}/AUC_{0-96}$ |
|---|---|---|---|
| Treatment A | 3.6 | 0.35 | 0.10 |
| Treatment B | 8.4 | 0.4 | 0.05 |
| Treatment C | 25.6 | 22.2 | 0.87 |

Table 7 shows the values of $AUC_{0-96}$ and $AUC_{0-6}$ the averaged data for all three treatments and the ratio $AUC_{0-6}/AUC_{0-96}$ as the extent of absorption to 6 hours. Six hours is considered the time of definite colon arrival since in fasted subjects the tablet will stay 0–2 hours in the stomach and 3±1 hours in the small intestine. We see that the extent of absorption to six hours for treatment A is 10%, for treatment B is 5% while for treatment C it is 87%. As expected the extent of absorption in the first six hours is much lower for the CDS tablets than for the commercial sulindac.

Results—Sulindac Sulfide and Sulindac Sulfone

Figure 2:
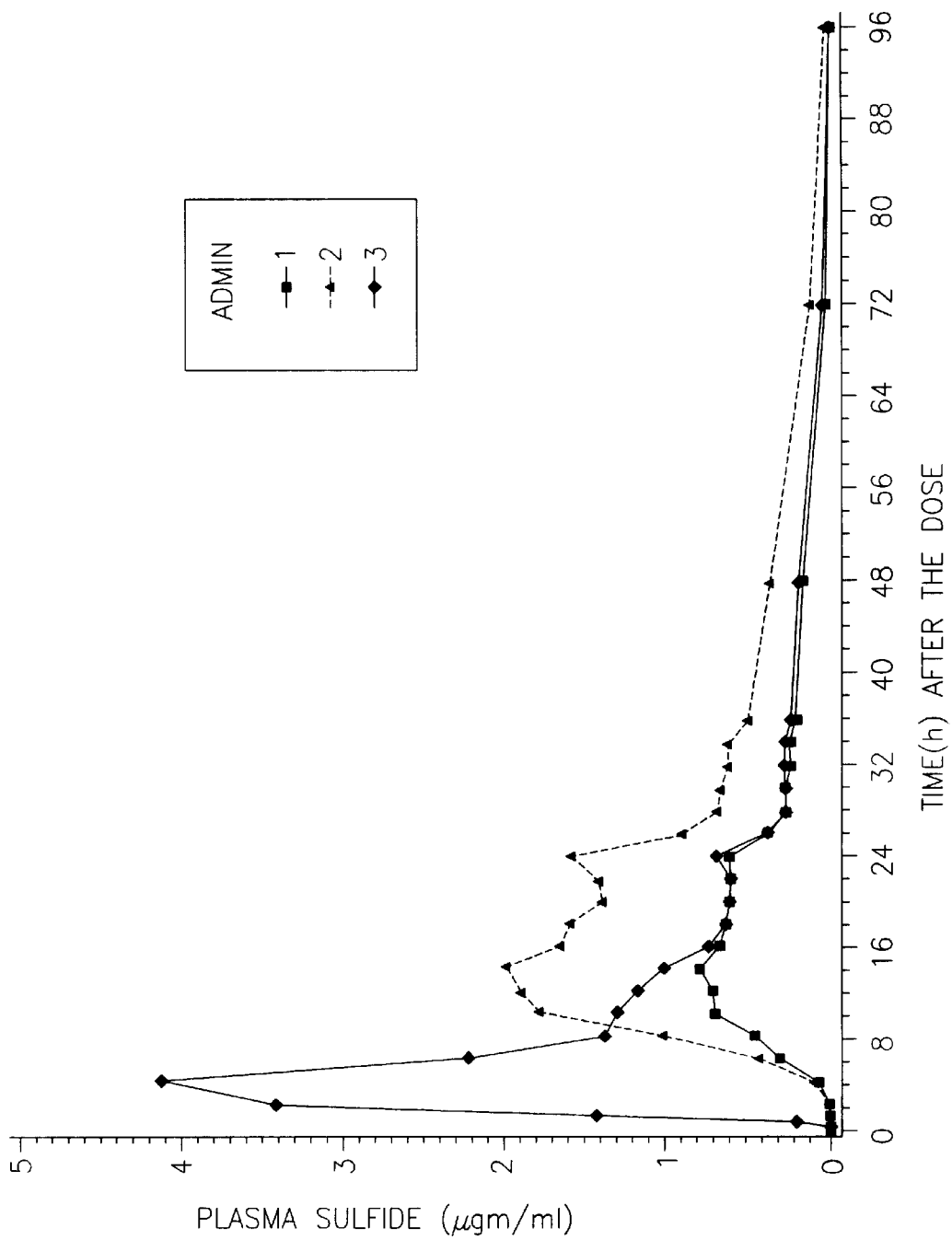
FIG. 2 shows the averaged data for the concentration of sulindac sulfide in the blood in the three treatments listed in the legend to FIG. 1.

The averaged data for the concentration of sulindac sulfide and sulindac sulfone in the blood are given in FIG. 2 and FIG. 3 respectively. The $t_{max}$ and $C_{max}$ values for the sulfide and sulfone for the individual volunteers are given in Tables 8 and 9 respectively while the AUC values are given in Tables 10 and 11 respectively.

TABLE 8

$C_{max}$ and $t_{max}$ for Sulindac Sulfide

| Volunteer No. | Treatment A $C_{max}$ ug/ml | Treatment A $t_{max}$ hours | Treatment B $C_{max}$ ug/ml | Treatment B $t_{max}$ hours | Treatment C $C_{max}$ ug/ml | Treatment C $t_{max}$ hours |
|---|---|---|---|---|---|---|
| 1 | 1.01 | 8 | 2.66 | 10 | 4.25 | 4 |
| 2 | 0.85 | 14 | 6.00 | 12 | 2.82 | 4 |
| 3 | 0.82 | 14 | 0.82 | 24 | 3.91 | 4 |
| 4 | 1.01 | 14 | 1.81 | 16 | 3.98 | 2 |
| 5 | 1.11 | 16 | 2.20 | 12 | 4.67 | 4 |
| 6 | 1.88 | 8 | 3.07 | 10 | 5.53 | 4 |
| 7 | 0.53 | 4 | 1.39 | 22 | 3.15 | 4 |
| 8 | 1.01 | 14 | 2.39 | 14 | 3.49 | 4 |
| 9 | 0.93 | 20 | 4.82 | 18 | 3.42 | 4 |
| 10 | 0.10 | 8 | 1.72 | 10 | 4.56 | 2 |
| 11 | 0.76 | 18 | 1.55 | 20 | 4.57 | 4 |
| 12 | 0.88 | 14 | 1.03 | 16 | 3.67 | 2 |
| 13 | 1.11 | 10 | 2.09 | 24 | 4.11 | 4 |
| 14 | 2.73 | 12 | 5.64 | 10 | 6.88 | 4 |
| 15 | 0.66 | 8 | 3.88 | 10 | 6.03 | 2 |
| 16 | 1.07 | 10 | 1.98 | 18 | 5.52 | 4 |
| 17 | 0.44 | 24 | 2.24 | 24 | 3.88 | 4 |
| 18 | 0.47 | 20 | 1.46 | 12 | 3.73 | 2 |
| Mean | 0.97 | 13.1 | 2.59 | 16.7 | 4.34 | 3.45 |
| Standard | 0.58 | 5.2 | 1.53 | 5.32 | 1.06 | 0.91 |
| Maximum | 2.73 | 24 | 6.00 | 24 | 6.88 | 4.0 |
| Minimum | 0.10 | 4 | 0.82 | 10 | 2.82 | 2.0 |

TABLE 9

$C_{max}$ and $t_{max}$ for Sulindac Sulfone

| Volunteer No. | Treatment A $C_{max}$ ug/ml | Treatment A $t_{max}$ hours | Treatment B $C_{max}$ ug/ml | Treatment B $t_{max}$ hours | Treatment C $C_{max}$ ug/ml | Treatment C $t_{max}$ hours |
|---|---|---|---|---|---|---|
| 1 | 0.40 | 24 | 0.80 | 22 | 1.76 | 4 |
| 2 | 0.48 | 16 | 2.11 | 16 | 1.02 | 4 |

TABLE 9-continued $C_{max}$ and $t_{max}$ for Sulindac Sulfone

| Volunteer No. | Treatment A | | Treatment B | | Treatment C | |
|---|---|---|---|---|---|---|
| | $C_{max}$ ug/ml | $t_{max}$ hours | $C_{max}$ ug/ml | $t_{max}$ hours | $C_{max}$ ug/ml | $t_{max}$ hours |
| 3 | 0.27 | 22 | 0.34 | 34 | 1.42 | 2 |
| 4 | 0.40 | 20 | 0.59 | 34 | 1.23 | 2 |
| 5 | 0.29 | 12 | 0.37 | 12 | 1.32 | 4 |
| 6 | 0.45 | 8 | 0.93 | 14 | 1.88 | 4 |
| 7 | 0.26 | 24 | 0.56 | 24 | 2.15 | 4 |
| 8 | 0.34 | 14 | 0.68 | 14 | 1.11 | 2 |
| 9 | 0.26 | 26 | 0.49 | 24 | 1.00 | 2 |
| 10 | 0.13 | 6 | 0.63 | 24 | 1.90 | 2 |
| 11 | 0.45 | 8 | 0.56 | 10 | 1.31 | 4 |
| 12 | 0.75 | 16 | 0.58 | 18 | 1.20 | 2 |
| 13 | 0.47 | 22 | 0.73 | 24 | 1.73 | 2 |
| 14 | 0.24 | 26 | 0.38 | 10 | 1.11 | 4 |
| 15 | 0.29 | 24 | 0.98 | 16 | 1.51 | 2 |
| 16 | 0.79 | 14 | 1.50 | 14 | 2.21 | 4 |
| 17 | 0.38 | 24 | 0.93 | 26 | 2.98 | 4 |
| 18 | 0.28 | 24 | 0.56 | 36 | 1.83 | 2 |
| Mean | 0.39 | 18.3 | 0.76 | 20.7 | 1.59 | 3.0 |
| Standard | 0.17 | 6.7 | 0.44 | 8.23 | 0.52 | 1.0 |
| Maximum | 0.79 | 26 | 2.11 | 36 | 2.98 | 4.0 |
| Minimum | 0.13 | 6 | 0.34 | 10 | 1.00 | 2.0 |

TABLE 10

$AUC_{0-96}$ for Sulindac Sulfide

| Volunteer No. | Treatment A $AUC_{0-96}$ (h)(μg/ml) | Treatment B $AUC_{0-96}$ (h)(μg/ml) | Treatment C $AUC_{0-96}$ (h)(μg/ml) |
|---|---|---|---|
| 1 | 11.45 | 35.75 | 27.76 |
| 2 | 20.49 | 72.60 | 46.94 |
| 3 | 18.61 | 21.62 | 42.25 |
| 4 | 17.62 | 39.54 | 32.99 |
| 5 | 20.89 | 13.23 | 36.37 |
| 6 | 39.80 | 40.66 | 56.49 |
| 7 | 11.88 | 26.70 | 21.95 |
| 8 | 25.00 | 54.75 | 46.22 |
| 9 | 17.53 | 103.55 | 37.73 |
| 10 | 1.98 | 39.32 | 44.40 |
| 11 | 16.28 | 36.34 | 38.87 |
| 12 | 14.78 | 27.07 | 29.87 |
| 13 | 21.92 | 40.08 | 41.97 |
| 14 | 80.74 | 161.51 | 139.21 |
| 15 | 10.17 | 59.64 | 46.48 |
| 16 | 13.87 | 35.96 | 34.69 |
| 17 | 19.53 | 69.70 | 45.66 |
| 18 | 13.17 | 25.44 | 35.63 |
| Mean | 20.87 | 50.19 | 44.75 |
| Standard | 16.79 | 35.38 | 24.96 |
| Maximum | 80.74 | 161.51 | 139.21 |
| Minimum | 1.98 | 13.23 | 21.95 |

TABLE 11

$AUC_{0-96}$ for Sulindac Sulfone

| Volunteer No. | Treatment A $AUC_{0-95}$ (h)(μg/ml) | Treatment B $AUC_{0-95}$ (h)(μg/ml) | Treatment C $AUC_{0-95}$ (h)(μg/ml) |
|---|---|---|---|
| 1 | 9.48 | 26.22 | 26.13 |
| 2 | 16.70 | 62.52 | 32.01 |
| 3 | 10.59 | 13.35 | 28.49 |
| 4 | 12.51 | 27.51 | 25.60 |
| 5 | 10.36 | 5.12 | 24.56 |
| 6 | 18.45 | 22.50 | 34.28 |
| 7 | 13.18 | 21.24 | 26.05 |

TABLE 11-continued $AUC_{0-96}$ for Sulindac Sulfone

| Volunteer No. | Treatment A $AUC_{0-95}$ (h)(μg/ml) | Treatment B $AUC_{0-95}$ (h)(μg/ml) | Treatment C $AUC_{0-95}$ (h)(μg/ml) |
|---|---|---|---|
| 8 | 13.97 | 27.68 | 34.63 |
| 9 | 10.29 | 19.50 | 24.10 |
| 10 | 2.45 | 19.14 | 32.96 |
| 11 | 12.98 | 24.00 | 25.33 |
| 12 | 16.62 | 26.33 | 24.21 |
| 13 | 22.19 | 30.91 | 42.36 |
| 14 | 10.81 | 18.49 | 24.54 |
| 15 | 9.74 | 36.51 | 32.52 |
| 16 | 23.27 | 39.07 | 39.14 |
| 17 | 22.19 | 54.22 | 66.55 |
| 18 | 11.14 | 26.83 | 35.41 |
| Mean | 13.72 | 27.84 | 32.16 |
| Standard | 5.349 | 13.67 | 10.23 |
| Maximum | 23.27 | 62.52 | 66.55 |
| Minimum | 2.45 | 5.12 | 24.10 |

The mean $t_{max}$±standard deviation for sulindac sulfide for the three treatments were 13.1±5.2, 16.7±5.3, and 3.45±0.91 hours respectively with ranges (maximum–minimum) of 24–4, 24–10, and 4–2 hours respectively. The $t_{max}$ values for the sulfone were 18.3±6.7, 20.7±8.2 and 3.01±1.02 with ranges of 26–6, 36–10, and 4–2 hours respectively.

The mean $C_{max}$ for sulindac sulfide for treatment A was 0.97±0.58 (μg/ml) with the values ranging from 2.73–0.10, for treatment B was 2.59±1.53 (μg/ml) with the values ranging from 6.0–0.82, while for treatment C the value was 4.34±1.06 (μg/ml) with the values ranging from 6.86–2.82. The mean $C_{max}$ values for the sulfone were 0.39±0.17, 0.76±0.44, and 1.59±0.52 with the values ranging from 0.79–0.13, 2.11–0.34, and 2.98–1.00 (μg/ml) respectively.

The average AUC from zero to 96 hours ($AUC_{0-96}$) for sulindac sulfide was 20.87±16.79 (h)(μg/ml) with values ranging from 80.74 to 1.98 for treatment A, 50.19±35.38 (h)(μg/ml) with values ranging from 161.51 to 13.23 for treatment B, and 44.75±24.96 (h)(μg/ml) with values ranging from 139.21 to 21.95.

The average AUC from zero to 96 hours ($AUC_{0-96}$) for the sulindac sulfone was 13.72±5.35 (h)(μg/ml) with values ranging from 23.27 to 2.45 for treatment A, 27.84±13.67 (h)(μg/ml) with values ranging from 62.52 to 5.12 for treatment B, 32.15±10.23 (h)(μg/ml) with values ranging from 66.55 to 24.10 for treatment C.

TABLE 12

Ratio of Metabolites Sulfide/Sulfone (averaged data)

| Time | Treatment A | Treatment B | Treatment C |
|---|---|---|---|
| 0 | — | — | — |
| 0.5 | — | — | 1.43 |
| 1 | — | — | 2.00 |
| 2 | — | — | 2.43 |
| 4 | 1.11 | 0.71 | 2.73 |
| 6 | 1.36 | 1.43 | 1.83 |
| 8 | 1.90 | 3.13 | 1.69 |
| 10 | 2.92 | 3.75 | 1.59 |
| 12 | 2.80 | 4.04 | 1.71 |
| 14 | 2.67 | 3.23 | 1.27 |
| 16 | 2.26 | 2.74 | 1.14 |
| 18 | 2.33 | 2.76 | 1.17 |
| 20 | 2.07 | 2.59 | 1.32 |
| 22 | 2.14 | 2.68 | 1.30 |
| 24 | 2.07 | 2.76 | 1.54 |
| 26 | 1.48 | 1.67 | 0.83 |

TABLE 12-continued

Ratio of Metabolites Sulfide/Sulfone (averaged data)

| Time | Treatment A | Treatment B | Treatment C |
|------|-------------|-------------|-------------|
| 28 | 1.50 | 1.67 | 0.77 |
| 30 | 1.25 | 1.35 | 0.75 |
| 32 | 1.30 | 1.59 | 0.88 |
| 34 | 1.30 | 1.35 | 0.86 |
| 36 | 1.00 | 1.19 | 0.63 |
| 48 | 1.18 | 1.25 | 0.91 |
| 72 | 1.25 | 1.43 | 1.25 |
| 96 | — | — | 0.00 |

Table 12 gives the ratio of the metabolites (sulfide/sulfone) as a function of time for each of the treatments. For treatment A, the ratio reaches a peak of 2.92 at 10 hours, for Treatment B 4.04 at 12 hours, while for the commercial sulindac preparation Treatment C, the ratio peaks at 2.73 at 4 hours.

The two CDS sulindac formulations, treatment A and treatment B, showed their maximal concentrations at times that correspond to colonic delivery. The residence time in the stomach in the fasted state is 0–2 hours while small intestinal transit time is 3–5 hours (Davis, S., el. al., *GUT* 27:886 (1986)) so that colonic arrival is expected between a minimum of three hours and a maximum of seven hours. A $t_{max}$ greater than 6 hours is therefore indicative of colonic absorption at the maximum. As seen in Table 5, the CDS formulations gave $t_{max}$ of 8.29 hours and 7 hours, indicating colonic delivery. The commercial sulindac gave a mean $t_{max}$ of less than 2 hours, clearly indicating upper GI absorption. The area under the concentration versus time curve to a given time point represents the amount of the drug absorbed up to that time point. The ratio of that area to the total area under the concentration curve give the percentage of total drug absorbed that was absorbed up to that point. As can be seen in Table 7 the CDS formulations show relatively low absorption of the drug up to six hours, 10% and 5% respectively while treatment C, the non colonic delivery treatment, shows 87% drug delivery before six hours. One can conclude that the CDS formulations gave efficient colonic delivery. The $C_{max}$ for the CDS formulations was considerably lower than for the commercial tablet. So was the AUC with 300 mg dosed through the CDS (treatment B) giving about ⅓ the AUC of 300 mg dosed from the commercial tablet. While one might at first glance interpret this to indicate poor absorption of the drug from the colon, an anlysis of the results of the metabolites proves this to be a wrong interpretation. The AUC of the metabolites are of similar magnitude for treatments B and C, both of which had a 300 mg dose. The sulindac sulfide is somewhat higher from the CDS formulation than the conventional tablet (50.2 vs. 44.8 (h)($\mu$g/ml)) while the sulfone is slightly lower (27.8 vs. 32.2 (h)($\mu$g/ml)). If the sulindac was not being absorbed in any form from the colon one would not be able to obtain the metabolites. One is forced to the conclusion that the sulindac is undergoing metabolism in the colon or colon wall and the metabolites are being absorbed and therefore found in the blood. While the $C_{max}$ for the sulindac sulfide from the commercial sulindac is somewhat higher than that for the CDS formulation this concentration is obtained for sulindac absorbed into the blood and metabolized in the liver. The concentration seen by cells in the colon, often the target of sulindac treatment, is no higher than the blood concentration. The CDS formulation, treatment B, delivers its sulindac to the colon where the sulindac is only partialy absorbed into the blood. The sulindac is metabolized in the colon and then absorbed. The concentration observed in the blood is the metabolite concentration after dilution to blood volume. It stands to reason that the concentration of the metabolite in the colon is considerably higher than that in the blood.

The metabolism of sulindac in the colon shows a preference for the sulindac sulfide over the sulindac sufone. For equivalent doses, treatment B shows a higher AUC for sulindac sulfide than treatment C and a lower AUC for the sulindac sulfone. The ratio of AUC-sulfide/AUC-sulfone for the CDS treatment B is 1.81 while the conventional tablet of treatment C gives a ratio of 1.39. Colonic delivery, with colonic metabolism, is giving preferential metabolism to the sulfide metabolite. This preferential metabolism is probably even more pronounced than these numbers indicate. Once in the blood it is known that sulindac sulfide can be further metabolized to sulindac sulfone while the sulindac sulfone is inert (Brogden R. N., et al., *Drugs* 16.97–114 (1978)). This can be seen in Table 12 where for treatment C the ratio of the average concentration of sulindac sulfide to sulindac sulfone peaks at a value of 2.73 at 4 hours and thereafter falls to values below one. The CDS treatment B shows a higher peak ratio of average sulindac sulfide to sulindac sulfone concentration of 4.04 at 12 hours after dosage. This ratio also falls due to metabolism of the sulindac sulfide to the sulindac sulfone along with elimination of both drugs from the body. The average sulindac sulfide concentration, however, stays higher than the average sulindac sulfone concentration at all time points, indicative of a continuing supply of the sulfide metabolite to the blood through metabolism of the parent sulindac in the colon.

Conclusion

It has been shown that the CDS formulations of sulindac prevent the release of sulindac in the upper GI tract and deliver the sulindac to the colon. It has been further shown that the sulindac that is delivered to the colon is metabolized in the colon to its major metabolites, sulindac sulfide and sulindac sulfone. This metabolism shows a preference for the sulindac sulfide over the sulindac sulfone. Some of the sulindac sulfone (perhaps most) is formed from the sulindac sulfide after absorption into the blood. It is inferred that the local concentration of sulindac sulfide is relatively high in the colon before absorption into the blood. Sulindac sulfide is the more active metabolite in processes that require inhibition of prostaglandin and especially in processes dependent on COX-2 inhibition. The CDS formulations described are a more efficient way of delivering the sulindac sulfide metabolite to the colon for treatment of colonic diseases such as polyps or colon cancer than conventional delivery.

What is claimed is:

1. A composition or drug delivery device for localized drug release in the colon, said composition or device comprising one or more drugs in a core, and a coating surrounding said core, said coating having an outer surface, wherein said coating comprises water insoluble hydrophilic particulate matter embedded in a water-insoluble carrier, such that when said composition or device enters the gastrointestinal tract, said particulate matter absorbs liquid, thus forming channels that interconnect said core with said outer surface of said coating, and through which channels, said one or more drugs are released into the colon, such that at least one of said drugs is preferentially metabolized to a more active metabolite in the colon.

2. The composition or device of claim 1, wherein at least one of said one or more drugs is a COX-2 specific inhibitor.

3. The composition or device of claim 1, wherein at least one of said one or more drugs is a COX-1 specific inhibitor.

4. The composition or device of claim 1, wherein at least one of said one or more drugs is an NSAID.

5. The composition or device of claim 4, wherein said NSAID is selected from the group consisting of anthranilic acids, aspirin (5-acetylsalicylic acid), azodisal sodium, carboheterocyclic acids, carprofen, chlorambucil, diclophenac, fenbufen, fenclofenac, fenoprofen, flufenamic acid, flurbiprofen, fluprofen, furosemide, gold sodium thiomalate, ibuprofen, indomethacin, indoprofen, ketoprofen, lonazolac, loxoprofen, meclofenamic acid, mefanamic acid, melphalan, naproxen, penicillamin, phenylacetic acids, proprionic acids, salicylic acids, salazosulfapyridine, sulindac, tolmetin, a pyrazolone butazone propazone NSAID, meloxicam, oxicams, piroxicam, feldene, piroxicam beta cyclodextran, tenoxicam, etodolac, and oxaprozin.

6. The composition or device of claim 5, wherein said NSAID is selected from the group consisting of sulindac, aspirin, paraacetamol, diclofenac, piroxicam, meloxicam, flurbiprofen, indomethacin, ibuprofen, and fenoprofen.

7. The composition or device of claim 6, wherein said NSAID is sulindac.

8. The composition or device of claim 1, wherein said device is coated with an enteric coating.

9. The composition or device of claim 1, wherein said hydrophilic particulate matter comprises calcium pectinate.

10. The composition or device of claim 9, wherein said device is coated with an enteric coating.

11. The composition or device of claim 1, wherein said water-insoluble carrier comprises a dimethylaminoethylmethacrylate/methylmethacrylate and butylmethacrylate copolymer, a copolymer based on neutral methacrylic acid esters and diethylaminoethyl methacrylate esters wherein the polymer is cationic in the presence of acids.

12. The composition or device of claim 11, wherein said device is coated with an enteric coating.

13. The composition or device of claim 1, wherein said hydrophilic particulate matter comprises calcium pectinate and said water-insoluble carrier comprises a dimethylaminoethylmethacrylate/methylmethacrylate and butylmethacrylate copolymer, a copolymer based on neutral methacrylic acid esters and diethylaminoethyl methacrylate esters wherein the polymer is cationic in the presence of acids.

14. The composition or device of claim 13, wherein said device is coated with an enteric coating.

15. A method for treating a patient with sulindac, said method comprising orally administering said sulindac to said patient in a composition or drug delivery device that shields the stomach and small intestine from said sulindac and maximizes the release of said sulindac in said patient's colon.

16. The method of claim 15, wherein said sulindac is metabolized into sulindac sulfide in said colon.

17. The method of claim 15, wherein said composition or device comprises a core, and a coating surrounding said core, said coating having an outer surface, wherein said coating comprises water insoluble hydrophilic particulate matter embedded in a water-insoluble carrier, such that when said composition or device enters the gastrointestinal tract, said particulate matter absorbs liquid, thus forming channels that interconnect said core with said outer surface of said coating, and through which channels, said sulindac is released into said colon.

18. The method of claim 16, wherein said composition or device is coated with an enteric coating.

19. The method of claim 16, wherein said hydrophilic particulate matter comprises calcium pectinate.

20. The method of claim 19, wherein said composition or device is coated with an enteric coating.

21. The method of claim 16, wherein said water-insoluble carrier comprises a dimethylaminoethylmethacrylate/methylmethacrylate and butylmethacrylate copolymer, a copolymer based on neutral methacrylic acid esters and diethylaminoethyl methacrylate esters wherein the polymer is cationic in the presence of acids.

22. The method of claim 21, wherein said composition or device is coated with an enteric coating.

23. The method of claim 16, wherein said hydrophilic particulate matter comprises calcium pectinate and said water-insoluble carrier comprises a dimethylaminoethylmethacrylate/methylmethacrylate and butylmethacrylate copolymer, a copolymer based on neutral methacrylic acid esters and diethylaminoethyl methacrylate esters wherein the polymer is cationic in the presence of acids.

24. The device of claim 23, wherein said device is coated with an enteric coating.

25. The method of claim 15 wherein said composition or device is a tablet or capsule.

26. The method of claim 25, wherein said tablet or capsule is coated with an enteric coating.

27. The method of claim 25, wherein said composition or device is a tablet.

28. The method of claim 27, wherein said tablet is a matrix tablet.

29. The method of claim 25, wherein said tablet or capsule releases said sulindac in a burst.

30. The method of claim 25, wherein said tablet or capsule releases said sulindac in a controlled fashion.

31. The method of claim 15, wherein said sulindac is encapsulated in a microsphere, a liposome, a nanosphere or a microemulsion.

32. The method of claim 15, wherein said sulindac is in the form of pellets or minitablets.

33. The method of any one of claims claim 15–32, wherein said patient is being treated for a colonic disease.

34. The method of claim 33, wherein said colonic disease is colon polyps or colon cancer.

35. The method claim 15, wherein said sulindac is administered by oral delivery to said patient.

36. The method of claim 35, wherein the dose of said sulindac that is administered to said patient is 2–500 mg daily for 1–12 months in single or divided doses.

37. The method of claim 15, wherein the dose of said sulindac that is administered to said patient is 2–500 mg daily chronically in single or divided doses.

38. A method for treating colon polyps or colon cancer in a patient in need of the same, said method comprising orally administering one or more NSAIDs to said patient in a composition or device that minimizes release of said one or more NSAIDs prior to said one or more NSAIDs reaching said patient's colon and that maximizes the release of said one or more NSAIDs in said patient's colon, wherein said composition or device comprises a coating surrounding a core that contains said one or more NSAIDs, wherein said coating has an outer surface, and wherein said coating comprises water-insoluble hydrophilic particulate matter embedded in a water-insoluble carrier, wherein said particulate matter absorbs liquid from said patient's gastrointestinal tract, thus forming channels that interconnect said core with said outer surface of said coating, and through which channels, said one or more NSAIDs are released into said colon.

39. The method of claim 38, wherein said NSAID is metabolized into a more active metabolite in said patient's colon.

40. The method of claim 38, wherein said at least one NSAID is a COX-2 specific inhibitor.

41. The method of claim 38, wherein said at least one NSAID is a COX-1 specific inhibitor.

42. The method of claim 38, wherein said at least one NSAID is selected from the group consisting of anthranilic acids, aspirin (5-acetylsalicylic acid), azodisal sodium, carboheterocyclic acids, carprofen, chlorambucil, diclophenac, fenbufen, fenclofenac, fenoprofen, flufenamic acid, flurbiprofen, fluprofen, furosemide, gold sodium thiomalate, ibuprofen, indomethacin, indoprofen, ketoprofen, lonazolac, loxoprofen, meclofenamic acid, mefanamic acid, melphalan, naproxen, penicillamin, phenylacetic acids, proprionic acids, salicylic acids, salazosulfapyridine, sulindac, tolmetin, a pyrazolone butazone propazone NSAID, meloxicam, oxicams, piroxicam, feldene, piroxicam beta cyclodextran, tenoxicam. etodolac, and oxaprozin.

43. A method of claim 42, wherein said at least one NSAID is selected from the group consisting of sulindac, aspirin, paraacetamol, diclofenac, piroxicam, meloxicam, flurbiprofen, indomethacin, ibuprofen, and fenoprofen.

44. The method of claim 43, wherein said at least one NSAID is sulindac.

45. The method of claim 38, wherein said patient is human.

46. The method of claim 45, wherein said composition or device is coated with an enteric coating.

47. The method of claim 45, wherein said hydrophilic particulate matter comprises calcium pectinate.

48. The method of claim 47, wherein said device is coated with an enteric coating.

49. The method of claim 45, wherein said water-insoluble carrier comprises a dimethylaminoethylmethacrylate/methylmethacrylate and butylmethacrylate copolymer, a copolymer based on neutral methacrylic acid esters and diethylaminoethyl methacrylate esters wherein the polymer is cationic in the presence of acids.

50. The method of claim 49, wherein said device is coated with an enteric coating.

51. The method of claim 45, wherein said hydrophilic particulate matter comprises calcium pectinate and said water-insoluble carrier comprises a dimethylaminoethylmethacrylate/methylmethacrylate and butylmethacrylate copolymer, a copolymer based on neutral methacrylic acid esters and diethylaminoethyl methacrylate esters wherein the polymer is cationic in the presence of acids.

52. The method of claim 51, wherein said device is coated with an enteric coating.

53. The method claim 38, wherein said NSAID is administered by oral delivery to said patient.

54. The method of claim 53, wherein the dose of said NSAID that is administered to said patient is 2–500 mg daily for 1–12 months in single or divided doses.

55. The method of claim 53, wherein the dose of said NSAID that is administered to said patient is 2–500 mg daily chronically in single or divided doses.

56. A method of administering sulindac to a patient, said method comprising rectally administering said sulindac to said patient in a composition or drug delivery device that comprises a coating surrounding a core that contains said sulindac, wherein said coating has an outer surface, and wherein said coating comprises water-insoluble hydrophilic particulate matter embedded in a water-insoluble carrier, wherein said particulate matter absorbs liquid from said patient's gastrointestinal tract, thus forming channels that interconnect said core with said outer surface of said coating, and through which channels, said sulindac is released into said colon.

57. A method for treating colon polyps or colon cancer in a patient in need of the same, said method comprising rectally administering one or more NSAIDs to said patient in a composition or device that comprises a coating surrounding a core that contains said one or more NSAIDs, wherein said coating has an outer surface, and wherein said coating comprises water-insoluble hydrophilic particulate matter embedded in a water-insoluble carrier, wherein said particulate matter absorbs liquid from said patient's gastrointestinal tract, thus forming channels that interconnect said core with said outer surface of said coating, and through which channels, said one or more NSAIDs are released into said colon.

58. A method for administering one or more NSAIDs to the colon of a patient in need of the same, said method comprising orally administering said one or more NSAIDs to said patient in a composition or device that minimizes release of at least said one or more NSAIDs in the stomach and small intestine of said patient and that maximizes the release of said one or more NSAIDs in said patient's colon, wherein said composition or device comprises a coating surrounding a core that contains said one or more NSAIDs, wherein said coating has an outer surface, and wherein said coating comprises water-insoluble hydrophilic particulate matter embedded in a water-insoluble carrier, wherein said particulate matter absorbs liquid from said patient's gastrointestinal tract, thus forming channels that interconnect said core with said outer surface of said coating, and through which channels, said one or more NSAIDs are released into said colon.

59. The method of claim 58, wherein said administration is for prophylactic purposes.

60. The method of claim 58, wherein said administration is for therapeutic purposes.

61. The method of any one of claims 58–60, wherein said patient is a human.

* * * * *